(12) United States Patent
Kawabata et al.

(10) Patent No.: US 8,939,373 B2
(45) Date of Patent: Jan. 27, 2015

(54) INFORMATION ACQUISITION DEVICE, MEASUREMENT SYSTEM, AND INFORMATION ACQUISITION METHOD

(75) Inventors: Yutaka Kawabata, Kyoto (JP); Fumito Hiramura, Kyoto (JP)

(73) Assignee: Arkray, Inc., Kyoto (JP)

( * ) Notice: Subject to any disclaimer, the term of this patent is extended or adjusted under 35 U.S.C. 154(b) by 86 days.

(21) Appl. No.: 13/583,303

(22) PCT Filed: Mar. 14, 2011

(86) PCT No.: PCT/JP2011/055877
§ 371 (c)(1),
(2), (4) Date: Oct. 2, 2012

(87) PCT Pub. No.: WO2011/115028
PCT Pub. Date: Sep. 22, 2011

(65) Prior Publication Data
US 2013/0200140 A1 Aug. 8, 2013

(30) Foreign Application Priority Data
Mar. 15, 2010 (JP) .................................. 2010-058382

(51) Int. Cl.
*G06K 7/10* (2006.01)
*G06F 17/40* (2006.01)
*A61B 5/145* (2006.01)
(Continued)

(52) U.S. Cl.
CPC ............ *G06F 17/40* (2013.01); *A61B 5/14532* (2013.01); *A61B 5/7495* (2013.01); *G06Q 10/06* (2013.01); *G06Q 50/22* (2013.01);
(Continued)

(58) Field of Classification Search
CPC ... G06K 7/10881; G06K 17/00; G02B 26/10; B01L 3/545
USPC ........................ 235/435, 454, 462.01, 462.13
See application file for complete search history.

(56) References Cited

U.S. PATENT DOCUMENTS

| 5,371,687 A | 12/1994 | Holmes et al. |
| 5,594,906 A | 1/1997 | Holmes et al. |

(Continued)

FOREIGN PATENT DOCUMENTS

| JP | 62-196773 A | 8/1987 |
| JP | 08-21838 A | 1/1996 |

(Continued)

OTHER PUBLICATIONS

International Search Report issued in corresponding International Patent Application No. PCT/JP2011/055877 dated Apr. 12, 2011.

*Primary Examiner* — Paultep Savusdiphol
(74) *Attorney, Agent, or Firm* — Morgan, Lewis & Bockius LLP

(57) ABSTRACT

An information acquisition device 10 includes a data acquisition unit 11 acquiring measurement data from an external measuring device 20; a code reading unit 12 reading a code to acquire the information represented by the code; and a data processing unit 13 that associates the information acquired by the code reading unit 12 with the measurement data acquired by the data acquisition unit 11. Medical measuring devices used to measure patient status can be suggested as the measuring device 20. In such a case, for example, codes representing identifiers that identify patients can be used as the code.

14 Claims, 12 Drawing Sheets

(51) Int. Cl.
*A61B 5/00* (2006.01)
*G06Q 10/06* (2012.01)
*G06Q 50/22* (2012.01)

(52) U.S. Cl.
CPC . *A61B2560/0456* (2013.01); *A61B 2562/0295* (2013.01)
USPC .............................. 235/462.13; 235/462.01

(56) References Cited

U.S. PATENT DOCUMENTS

| | | | |
|---|---|---|---|
| 6,413,213 B1 | 7/2002 | Essenpreis et al. | |
| 7,860,583 B2* | 12/2010 | Condurso et al. | 700/2 |
| 8,449,480 B2* | 5/2013 | Fowler et al. | 600/583 |
| 2002/0060247 A1* | 5/2002 | Krishnaswamy et al. | 235/472.01 |
| 2005/0086071 A1* | 4/2005 | Fox et al. | 705/2 |
| 2005/0086072 A1* | 4/2005 | Fox et al. | 705/2 |
| 2006/0047538 A1* | 3/2006 | Condurso et al. | 705/3 |
| 2008/0091085 A1* | 4/2008 | Urushihata et al. | 600/300 |
| 2008/0221930 A1* | 9/2008 | Wekell et al. | 705/3 |
| 2009/0231124 A1* | 9/2009 | Klabunde et al. | 340/539.12 |
| 2010/0036407 A1* | 2/2010 | Fowler et al. | 606/181 |
| 2010/0041968 A1* | 2/2010 | Meschisen et al. | 600/301 |
| 2010/0268052 A1* | 10/2010 | Asama et al. | 600/365 |
| 2011/0204133 A1* | 8/2011 | Sakata | 235/375 |
| 2012/0046203 A1* | 2/2012 | Walsh et al. | 506/39 |

FOREIGN PATENT DOCUMENTS

| | | |
|---|---|---|
| JP | 08-240589 A | 9/1996 |
| JP | 2002-521692 A | 7/2002 |
| JP | 2003-215122 A | 7/2003 |
| JP | 2003-526108 A | 9/2003 |
| JP | 2005-169111 A | 6/2005 |
| JP | 2005-353045 A | 12/2005 |
| JP | 2007-212391 A | 8/2007 |
| KR | 10-2009-0104910 A | 10/2009 |
| WO | 00/07013 A2 | 2/2000 |
| WO | 01/67079 A1 | 9/2001 |
| WO | 2006/046588 A1 | 5/2006 |
| WO | 2009/081790 A1 | 7/2009 |
| WO | 2009/099148 A1 | 8/2009 |

* cited by examiner

FIG. 4

(a) Identification information

```
Patient A ID:01234              |||　||||
Patient B ID:12456              ||　|||　|||
Patient C ID:24356              ||||||　||| measurement operator X ID:54678   |||||||||||
measurement operator Y ID:55679   |　|||　||||||
measurement operator Z ID:56898   |||　|　||||
```

(b) Health information

```
[Item]                    [Numerical Value]
Preprandial   |||||||||   150 cm or less  ||||||||||||||   45 kg or less  ||||||||||||||
Postprandial  |||||||||   150-155 cm      ||||||||||||||   45-50 kg       ||||||||||||||
Body weight   |||||||||   155-160 cm      ||||||||||||||   50-55 kg       ||||||||||||||
Body height   |||||||||   160-165 cm      ||||||||||||||   55-60 kg       ||||||||||||||
                          165-170 cm      ||||||||||||||   60-65 kg       ||||||||||||||
                          170-175 cm      ||||||||||||||   65-70 kg       ||||||||||||||
                          175-180 cm      ||||||||||||||   70-75 kg       ||||||||||||||
                          180-185 cm      ||||||||||||||   75-80 kg       ||||||||||||||
                          185 cm or more  ||||||||||||||   80-85 kg       ||||||||||||||
                                                           85 kg or more  ||||||||||||||
```

(c) Use-by date information

```
Sensor use-by date              ||||||||||||||||
 20100930

Reference solution use-by date  ||||||||||||||||
 20200725
```

INFORMATION ACQUISITION DEVICE, MEASUREMENT SYSTEM, AND INFORMATION ACQUISITION METHOD

CROSS-REFERENCE TO RELATED APPLICATION

This application is the U.S. National Phase under 35 U.S. §371 of International Application PCT/JP2011/055877, filed on Mar. 14, 2011, Which claims priority to JP Application No. 2010-058382, filed on Mar. 15, 2010, the contents of which are herein incorporated by reference in their entireties.

TECHNICAL FIELD

The present invention relates to an information acquisition device that acquires data measured by a measuring device, a measurement system utilizing the same, and an information acquisition method.

BACKGROUND ART

In recent years, various parameters, e.g. blood glucose levels, body temperature, pulse, blood pressure, and the like, have been measured in patients in healthcare settings for the purpose of managing the physical condition of the patients. Data obtained by such measurements is gathered for every patient, stored in a database, and used for diagnostic purposes by physicians. Management in database form is particularly important for blood glucose levels, which have to be measured several times a day for every single patient.

In addition, when such data management is performed, local physicians or medical personnel have to process data so as to associate data obtained by measurement with patient-identifying data, for example, process patient IDs, etc. by registering them in conjunction with data obtained from a measuring device. However, such processing places a burden on the physicians and medical personnel. For this reason, measuring devices have been proposed that can acquire both measurements and patient information and then associate them to create a unitary data item (for example, see Patent Documents 1 and 2).

Specifically, Patent Documents 1 and 2 have disclosed measuring devices equipped with barcode readers. The measuring devices disclosed in Patent Documents 1 and 2 are glucometers provided with a slot for inserting a sensor to which a blood sample drop is applied. The glucometers measure blood glucose levels when a sensor is inserted in the slot. In addition, the measuring devices disclosed in Patent Document 1 and 2 are equipped with barcode readers and are capable of acquiring data represented by barcodes. Patient IDs, operator (physician or medical personnel) IDs, and other data related to measurement data is suggested as the data represented by barcodes.

Furthermore, the measuring devices disclosed in Patent Documents 1 and 2 handle blood glucose levels acquired from sensors and patient IDs, etc. read by the barcode readers as unitary data items and can transmit them to an external computer operating as a database. In particular, Patent Document 1 has disclosed a docking station for a measuring device. The docking station has a function, in accordance with which, upon connecting a measuring device, the station automatically acquires data and transmits the acquired data to an external computer. In this case, the only thing a physician or other medical personnel needs to do is connect a measuring device that has completed measurements to the docking station.

In addition, Patent Document 1, in particular, has disclosed an example, in which data represented by barcodes indicates sensor expiration dates. In this example, a measuring device uses an expiration date it reads to determine whether a sensor is functional and alerts the operator of the measuring device if the sensor is not functional. As a result, faulty measurements due to passage of sensor expiration dates can be minimized.

CITATION LIST

Patent Document

Patent Document 1: Japanese translation of PCT International Application Publication No. 2002-521692.
Patent Document 2: Japanese translation of PCT International Application Publication No. 2003-526108.

DISCLOSURE OF THE INVENTION

Problem to be Solved by the Invention

The use of the measuring devices disclosed in the above-mentioned Patent Documents 1 or 2 can alleviate the burden imposed on the physicians and medical personnel. However, the measuring devices disclosed in Patent Documents 1 and 2 suffer from the following problems.

First, one of the problems is that the measuring devices used at medical institutions and patient homes would have to be replaced with the measuring devices disclosed in Patent Document 1 or 2, thereby incurring additional costs. In addition, the measuring devices disclosed in Patent Document 1 and 2 are more expensive than conventional measuring devices, which are not equipped with barcode readers. Furthermore, because of the increased size and weight of the measuring devices, poor operability is also a problem.

Furthermore, despite the fact that Patent Document 1 has disclosed a technology that minimizes faulty measurements by issuing alerts to operators based on sensor expiration dates, this technology does not sufficiently avoid situations producing faulty measurement results.

An exemplary object of the present invention is to provide an information acquisition device that eliminates the above-described problems and is capable of using conventional measuring devices while associating measurement data with data related thereto in a simple manner, as well as a measurement system utilizing the same and an information acquisition method.

Means for Solving the Problems

In order to attain the above-described object, the information acquisition device of the present invention is characterized by being provided with a data acquisition unit that acquires measurement data from an external measuring device, a code reading unit that reads a code to acquire the information represented by the code, and a data processing unit that associates the information acquired by the code reading unit with the measurement data acquired by the data acquisition unit.

Based on the above-described features, the information acquisition device of the present invention is capable of acquiring measurement data from conventional measuring devices and new measuring devices configured in conformance with the information acquisition device (configured to permit data communication with the information acquisition device). In addition, even if the configuration of the measuring device does not conform to the information acquisition device, the information acquisition device of the present invention is capable of acquiring measurement data from the measuring device if retrofit parts or devices can be used to enable transmission of measurement data from the measuring device to the information acquisition device.

Further, according to the information acquisition device of the present invention, barcodes and other codes representing data related to measurement data (for example, medical practitioner IDs, patient IDs, sensor Lot. Nos., etc.), are prepared in advance and if operators read these codes using the code reading unit, the measurement data is automatically associated with the related data. Thus, in accordance with the present invention, the cost increase is also minimized because data association can be performed in a simple manner using conventional measuring devices without introducing new measuring devices.

If the external measuring device is a medical measuring device used to measure patient status, then the code used in the above-described information acquisition device of the present invention is at least one type of codes selected from codes representing identifiers that identify medical practitioners and codes representing identifiers that identify patients.

In addition, in a preferred implementation of the above-described information acquisition device of the present invention, if the external measuring device can perform measurement of target components in samples and accuracy testing of reference solutions used for the measurement of the target components with sensors, and, furthermore, the codes used are codes representing a first use-by date set for the sensors and codes representing a second use-by date set for the reference solutions, then the code reading unit acquires the first use-by date and second use-by date and the data processing unit determines whether or not at least one of the first use-by date and second use-by date acquired by the code reading unit has expired and, if it has expired, exercises control intended to ensure that no processing of sample-related measurement data is performed in said information acquisition device, issues an outbound notification, or does both.

This avoids situations that produce faulty actual measurement results. In addition, when faulty measurement results were produced in the past, it was difficult to determine whether the problem stemmed from the measuring device or whether there was a problem with the sensors and reference solutions. The above-described implementation, however, makes it possible to carry out such a determination in a simple manner.

In this Specification, the term "control intended to ensure that no processing is performed in said information acquisition device" refers to control intended to ensure that the measurement mode in the information acquisition device is not executed, namely, for example, control intended to ensure that no acquisition of measurement data from the external measuring device is performed by the data acquisition unit; control intended to ensure that the code reading unit is not allowed to read codes; control intended to ensure that the data processing unit itself does not perform association of information; or control that combines two or more of the above-mentioned types of control, etc. In addition, in this Specification, an alert issued to the operator of the information acquisition device is suggested as the "outbound notification".

In addition, in the above-described implementation, when the data acquisition unit acquires reference solution-related measurement data output by the measuring device during accuracy testing, the data processing unit preferably further determines whether or not the reference solution-related measurement data meets preset conditions and exercises control intended to ensure that no processing of sample-related measurement data is performed in said information acquisition device, issues an outbound notification, or does both if the reference solution-related measurement data does not meet the preset conditions. In such a case, situations producing faulty actual measurement results are avoided in a more reliable manner.

In addition, in the present invention, when used with respect to reference solution-related measurement data, the term "preset condition" indicates a condition that ensures that a reference solution can be used as a standard for measuring target components. The correct concentration level of a target component in a reference solution is suggested as an example of such a "preset condition".

In addition, in the above-described case, if neither the first use-by date nor the second use-by date has expired and, at the same time, the reference solution-related measurement data meets the preset conditions, it is particularly preferable for the data processing unit to issue an outbound notification to that effect.

Furthermore, in the above-described case, it is also particularly preferable for the data processing unit to exercise control intended to ensure that processing of the sample-related measurement data is carried out in said information acquisition device if neither the first use-by date nor the second use-by date has expired and, at the same time, the reference solution-related measurement data meets the preset conditions.

In addition, in another preferred implementation of the information acquisition device of the present invention, if the codes used are codes representing sensor identification information utilized for sensor identification, the code reading unit acquires the sensor identification information and the data processing unit determines whether or not the sensor identified by the acquired sensor identification information can be used in the measuring device and exercises control intended to ensure that the processing of the sample-related measurement data is performed in said information acquisition device if the sensor can be used in the measuring device, or exercises control intended to ensure that no processing is performed in said information acquisition device, issues an outbound notification, or does both if the sensor cannot be used in the measuring device.

Furthermore, in the first-mentioned implementation, the data processing unit preferably exercises control intended to ensure that no processing of the sample-related measurement data is performed in said information acquisition device, issues an outbound notification, or does both if at least one of the following applies, that is, if the code reading unit cannot acquire the first use-by date, if the code reading unit cannot acquire the second use-by date, if the data acquisition unit cannot acquire the reference solution-related measurement data, or if the data acquisition unit can acquire no sample-related measurement data.

In addition, in the first-mentioned implementation, said information acquisition device is preferably adapted to enable operation involving switching between operational modes, including a quality control mode, and, if the operational mode is set to the quality control mode, the data processing unit determines whether or not at least one date selected from the first use-by date and second use-by date acquired by the code reading unit has expired. If the information acquisition device of the present invention is implemented on a computer, such operational mode switching can be implemented, for example, with a software program installed on the computer.

In another preferred implementation of the above-described information acquisition device of the present invention, the data processing unit associates dummy data with the measurement data acquired by the data acquisition unit if the code reading unit cannot acquire the information. In addition, in another preferred implementation of the above-described information acquisition device of the present invention, the information acquisition device is provided with a display unit for external presentation of information.

In a preferred implementation of the above-described information acquisition device of the present invention, the code reading unit reads multiple codes representing different information items to acquire the information represented by each respective code and the data processing unit associates the acquired multiple information items with the measurement data. This implementation provides an improvement in user convenience (including that of operators and managers).

In addition, in another preferred implementation of the above-described information acquisition device of the present invention, the codes used are multiple barcodes and the number of digits in each one of the multiple barcodes is determined by the type of information represented by said barcode. This implementation facilitates data management.

Furthermore, in another preferred implementation of the above-described information acquisition device of the present invention, the data acquisition unit is capable of acquiring new measurement data from a measuring device other than the above-mentioned measuring device. In accordance with this implementation, in case of a measuring device failure, the failed measuring device can be replaced with another measuring device. In addition, in the above-described implementation, the principles of measurement used in said other measuring device may differ from the principles of measurement used in said measuring device. Furthermore, in the above-described implementation, the data processing unit preferably further associates the new measurement data with the measurement data, with which the information has already been associated. In this case, an improvement in user convenience (including that of operators and managers) is also achieved.

In another preferred implementation, the above-described information acquisition device of the present invention is provided with an input receiving unit receiving external information input and the data processing unit associates information received by the input receiving unit with the measurement data. The use of this implementation also provides an improvement in user convenience (including that of operators and managers).

In addition, the above-described information acquisition device of the present invention is preferably adapted to be connectable to a docking station that enables data communication with external computers. In such a case, associated measurement data can be collected and managed in a simple way.

In addition, in order to attain the above-described object, the measurement system of the present invention is devised as a measurement system comprising a measuring device and an information acquisition device, with said information acquisition device comprising: a data acquisition unit that acquires measurement data from the measuring device, a code reading unit that acquires information represented by the codes, and a data processing unit that associates the information acquired by the code reading unit with the measurement data acquired by the data acquisition unit.

In a preferred implementation, the above-described measurement system further comprises a docking station that enables data communication between the information acquisition device and external computers and the information acquisition device is adapted to be connectable to the docking station.

Furthermore, in order to attain the above-described object, the information acquisition method of the present invention is devised as an information acquisition method utilizing a measuring device and codes that represent specific information and comprises the steps of (a) acquiring measurement data from the measuring device; (b) reading the codes and acquiring the information represented by the codes; and (c) associating the information acquired in Step (b) with the measurement data acquired in Step (a).

If the measuring device in the above-mentioned information acquisition method of the present invention is a medical measuring device used to measure patient status, then the codes used are at least one type of codes selected from the codes representing identifiers that identify medical practitioners and the codes representing identifiers that identify patients.

In a preferred implementation of the above-mentioned information acquisition method of the present invention, the measuring device can perform measurement of target components in samples and accuracy testing of reference solutions used for measuring the target components with sensors, and furthermore, if the codes used are codes representing a first use-by date set for the sensors and codes representing a second use-by date set for the reference solutions, the method further includes the steps of: (d) reading the codes representing the first use-by date and the codes representing the second use-by date and acquiring the first use-by date and second use-by date and (e) determining whether the first use-by date and second use-by date acquired in Step (d) have expired, Steps (d) and (e) are executed prior to the execution of Steps (a) and (b), and the execution of at least one step among Steps (a) through (c) is halted, an outbound notification is issued, or both operations are carried out if it is determined in Step (e) that at least one of the first use-by date and second use-by date has expired. Furthermore, in the above-described implementation, it is particularly preferable to halt the execution of at least one step selected from Step (a) and Step (b), issue an outbound notification, or do both if it is determined in Step (e) that at least one of the first use-by date and second use-by date has expired.

In addition, particularly preferably, the above-described implementation further includes the steps of: (f) acquiring reference solution-related measurement data output by the measuring device during accuracy testing and (g) determining whether or not the reference solution-related measurement data acquired in Step (f) meets the preset conditions, Steps (f) and (g) are executed prior to the execution of Steps (a) and (b), and, if it is determined in Step (g) that the measurement data acquired in Step (f) does not meet the preset conditions, the execution of at least one step among Steps (a) through (c) is halted, an outbound notification is issued, or both operations are carried out.

In addition, in the above-described case, if (h) it is determined in Step (e) that neither the first use-by date nor the second use-by date has expired and, at the same time, if it is determined in Step (g) that the preset conditions have been met, the method preferably further comprises issuing an outbound notification to that effect.

In addition, in the above-described case, it is preferable for Steps (a) through (c) to be executed if it is determined in Step (e) that there has been no expiration and, at the same time, if it is determined in Step (g) that the preset conditions have been met.

In addition, in another preferred implementation of the above-described information acquisition method of the present invention, if the codes used are codes representing sensor identification information utilized for sensor identification, the method further comprises the steps of: (j) reading the codes representing the sensor identification information to acquire the sensor identification information and (k) determining whether or not the sensor identified by the sensor identification information acquired in Step (j) can be used in the measuring device, Steps (j) and (k) are executed prior to the execution of Steps (a) and (b), and, if it is determined in Step (k) that the sensor can be used in the measuring device, Steps (a) through (c) are carried out, and, on the other hand, if it is determined in Step (k) that the sensor cannot be used in the measuring device, the execution of at least one step among Steps (a) through (c) is halted, an outbound notification is issued, or both operations are carried out. Furthermore, in this implementation, it is particularly preferable to halt the execution of at least one step selected from Step (a) and Step (b), issue an outbound notification, or do both if it is determined in Step (k) that the sensor cannot be used in the measuring device.

In addition, in the first-mentioned implementation, it is also preferable to halt the execution of at least one step among Steps (a) through (c), issue an outbound notification, or do both if at least one of the following applies, that is, if no first use-by date can be acquired in Step (d), if no second use-by date can be acquired in Step (d), or if no reference solution-related measurement data can be acquired in Step (f). Furthermore, if one of the above-described conditions applies, it is particularly preferable to halt the execution of at least one step selected from Step (a) and Step (b), issue an outbound notification, or do both.

In another preferred implementation of the above-described information acquisition method of the present invention, in Step (c), dummy data is associated with the measurement data acquired in Step (a) if the information could not be acquired in Step (b).

Furthermore, in another preferred implementation of the above-described information acquisition method of the present invention, in Step (b), the multiple codes representing different information items are read to acquire the information represented by each respective code and, in Step (c), the acquired multiple information items are associated with the measurement data.

In addition, even more preferably, the codes used are multiple barcodes and the number of digits in each one of the multiple barcodes is determined by the type of information represented by said barcode.

Furthermore, in another preferred implementation of the above-described information acquisition method of the present invention, if multiple measuring devices are used, in Step (a), the measurement data is acquired from each one of the multiple measuring devices and, in Step (c), each one of the measurement data items acquired from the multiple measuring devices is associated with the same information acquired in Step (b).

In another preferred implementation, the above-described information acquisition method of the present invention further comprises (l) receiving external information input and, in Step (c), the information received in Step (l) is associated with the measurement data.

In addition, in another preferred implementation, the above-described information acquisition method of the present invention further comprises (m) transferring the measurement data with which the information was associated in Step (c) to an external computer.

Furthermore, in order to attain the above-described object, the first software program of the present invention is devised as a software program intended to be used on a computer for information acquisition using measurement units that measure a target component, codes representing specific information, and a code reading unit capable of reading the codes, causes a computer to execute the steps of (a) acquiring measurement data from the measurement units; (b) directing the reading unit to carry out the reading of the codes to acquire the information represented by the codes; and (c) associating the information acquired in Step (b) with the measurement data acquired in Step (a).

Further, in addition to the above-described object, a second object is to provide a measuring device capable of avoiding situations that produce faulty measurement results, a quality control method therefor, and a software program used to implement them.

In order to achieve the above-mentioned second object, the measuring device of the present invention can use sensors to carry out measurement of target components in samples and accuracy testing of reference solutions used for measuring the target components and is provided with a measurement unit that carries out measurements with sensors to acquire measurement data, a code reading unit that reads codes to acquire the information represented by the codes, and a data processing unit, with the data processing unit having at least one of function (I) shown below and function (II) shown below.

(I) A function, in accordance with which the codes used are codes representing a first use-by date set for sensors and codes representing a second use-by date set for reference solutions, and, upon acquisition of the first use-by date and second use-by date, the code reading unit determines whether or not the first use-by date and second use-by date has expired and, if at least one of the first use-by date and second use-by date has expired, exercises control such that no measurement of target components in samples is performed by the measurement units, issues an outbound notification, or does both.

(II) A function in accordance with which, upon carrying out accuracy testing and acquiring reference solution-related measurement data, the measurement units determine whether or not the acquired reference solution-related measurement data meets preset conditions and, if the reference solution-related measurement data does not meet the preset conditions, exercises control such that no measurement of target components in samples is performed by the measurement units, issues an outbound notification, or does both.

Based on the above-described features, the measuring device of the present invention can avoid situations producing faulty measurement results. In addition, when faulty measurement results were produced in the past, it was difficult to determine whether the problem stemmed from the measuring device or whether there was a problem with the sensors and reference solutions. The above-described implementation, however, makes it possible to carry out such a determination in a simple manner.

In the above-described implementation, particularly preferably, the data processing unit possesses both the above-described function (I) and the above-described function (II) and, if neither the first use-by date nor the second use-by date has expired and, at the same time, the reference solution-related measurement data meets the preset conditions, the data processing unit directs the measurement units to measure target components in samples.

In addition, in another preferred implementation of the above-described measuring device of the present invention, when the codes used are codes representing sensor identification information utilized for sensor identification, the code reading unit acquires the sensor identification information, the data processing unit determines whether or not the sensor identified by the acquired sensor identification information can be used in the measurement units and, if the sensor can be used in the measurement units, exercises control such that measurement of target components in samples is performed by the measurement units, and, on the other hand, if the sensor cannot be used in the measuring device, exercises control such that no measurement of target components in samples is performed by the measurement units, issues an outbound notification, or does both.

Furthermore, in another preferred implementation of the above-described measuring device of the present invention, if at least one of the following applies, i.e., if the code reading unit cannot acquire the first use-by date, if the code reading unit cannot acquire the second use-by date, and if the measuring units cannot acquire the reference solution-related measurement data, the data processing unit exercises control such that no measurement of target components in samples is performed by the measuring units, issues an outbound notification, or does both.

In addition, in order to attain the above-mentioned second object, the quality control method of the present invention includes at least one of the following Step (a) and Step (b) intended for the quality control of the sensors used for measuring device measuring target components in samples and reference solutions used for measuring the target components.

(a) A step, during which the code reading unit capable of reading codes representing specific information is used to read codes representing a first use-by date set for the sensors and codes representing a second use-by date set for the reference solutions and acquire a first use-by date and a second use-by date, the data processing unit is used to determined whether or not the first use-by date and second use-by date has expired, and, if it is determined that at least one of the first use-by date and second use-by date has expired, the data processing unit carries out processing to disallow the measurement of the target component in the samples by the measuring device, issues an outbound notification, or does both.

(b) A step, during which the measuring units that carry out measurements using sensors are used to measure the reference solutions, the data processing unit is used to determine whether or not the reference solution-related measurement data meets preset conditions, and, if it is determined that the reference solution-related measurement data does not meet the preset conditions, the data processing unit carries out processing to disallow measurement of the target component in the samples by the measuring device, issues an outbound notification, or does both.

Furthermore, in the above-described implementation, it is particularly preferable for said quality control method to include both Step (a) and Step (b) and for processing that authorizes measurement of the target component in the samples by the measuring device to be carried out only if in Step (a) it is determined that both the first use-by date and second use-by date have not expired and, at the same time, in Step (b), it is determined that the reference solution-related measurement data meets the preset conditions.

In addition, in a preferred implementation, the above-described quality control method of the present invention further includes (c) using the code reading unit to read codes representing sensor identification information utilized for sensor identification and acquire the sensor identification information and (d) determining whether or not the sensor identified by the sensor identification information acquired in Step (c) can be used in the measuring device and, if it is determined in Step (d) that the sensor can be used in the measuring device, the measurement of target components in the samples is authorized, and, on the other hand, if it is determined in Step (d) that the sensor cannot be used in the measuring device, processing is carried out to disallow the measurement of the target component in the samples by the measuring device, an outbound notification is issued, or both operations are performed.

Furthermore, in the above-described quality control method of the present invention, it is also preferable to disallow the measurement of the target component in the samples by the measuring device, issue an outbound notification, or do both if at least one of the following applies, i.e., if no first use-by date can be acquired in Step (a), if no second use-by date can be acquired in Step (a), or if no reference solution-related measurement data can be acquired in Step (b).

Furthermore, in order to achieve the above-described second object, the software program of the present invention, which is devised as a software program intended to be used on a computer for the quality control of sensors used in a measuring device measuring target components in samples and reference solutions used for measuring the target components, causes a computer to execute the steps of: (a) directing measuring units that perform sensor-based measurements to carry out measurements using sensors having a drop of a reference solution applied thereto; (b) directing the code reading unit capable of reading codes representing specific information to read codes representing a first use-by date set for the sensors and codes representing a second use-by date set for the reference solutions to acquire the first use-by date and second use-by date; (c) determining whether or not the first use-by date and second use-by date acquired in Step (b) have expired, and (d) if in Step (c) it is determined that at least one of the first use-by date and second use-by date has expired, carrying out processing to disallow measurement of the target components by the measuring device with sensors having a sample drop applied thereto, issuing an outbound notification, or performing both operations.

Effects of the Invention

Based on the above features, the present invention permits use of conventional measuring devices and, furthermore, makes it possible to associate measurement data with data related thereto in a simple manner.

BRIEF DESCRIPTION OF THE DRAWINGS

FIGS. 4 (a)-(c) are diagrams illustrating exemplary codes used in Embodiment 1 of the present invention. FIG. 4 (a) illustrates codes representing identification information, FIG. 4 (b) illustrates codes representing health information, and FIG. 4 (c) shows codes representing use-by date information.

DESCRIPTION OF EMBODIMENTS (Embodiment 1)

Figure 1:
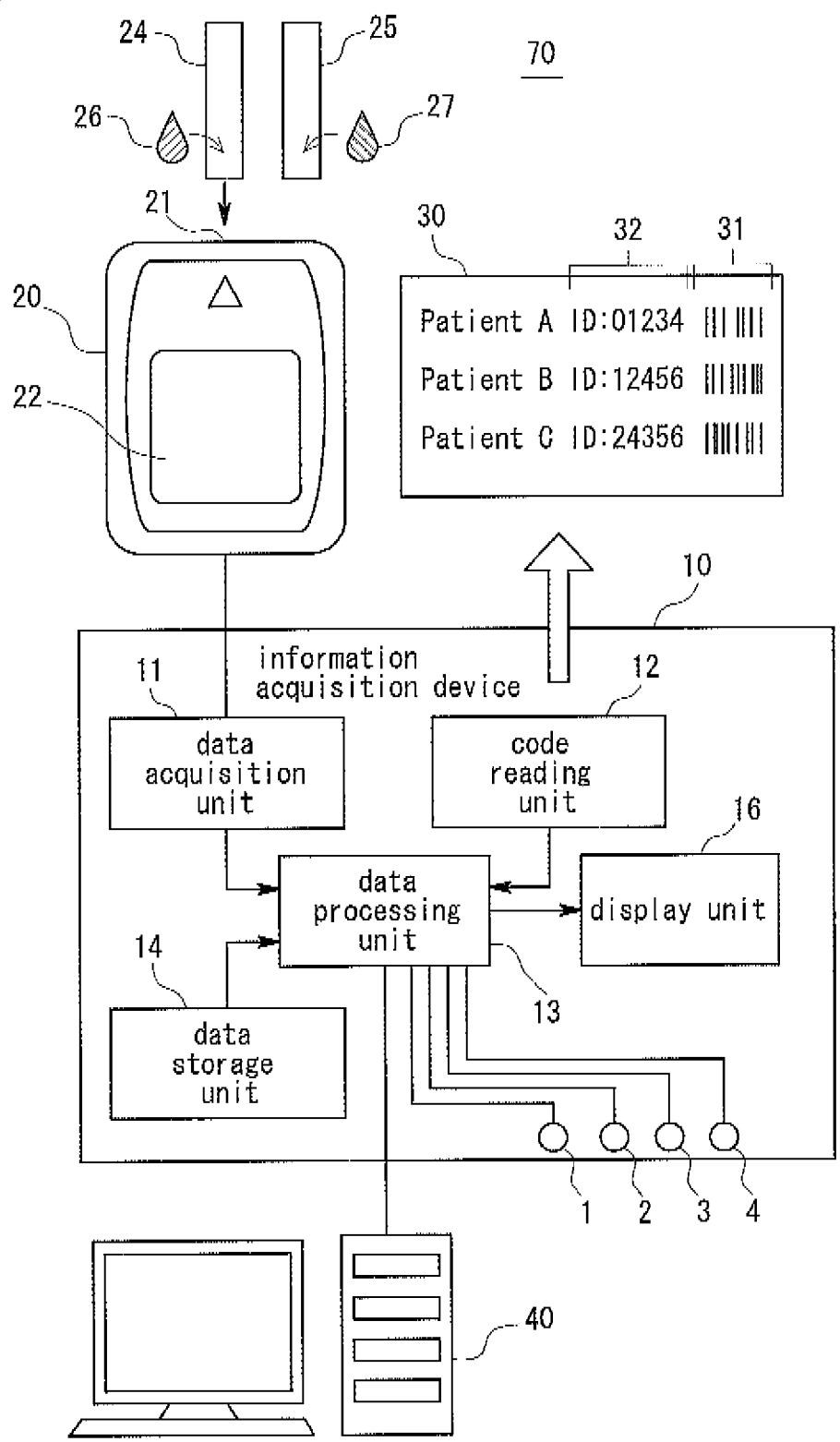
FIG. 1 is a block diagram illustrating the configuration of the information acquisition device used in Embodiment 1 of the present invention.

Below, the information acquisition device, measurement system, information acquisition method, and software program used in Embodiment 1 of the present invention will be described with reference to FIG. 1-FIG. 7. First of all, the configuration of the information acquisition device 10 and the measurement system 70 used in Embodiment 1 will be described with reference to FIG. 1. FIG. 1 is a block diagram illustrating the configuration of the information acquisition device used in Embodiment 1 of the present invention.

As shown in FIG. 1, the information acquisition device 10 forms part of the measurement system 70 along with a measuring device 20. In this embodiment, as long as the measuring device 20 has a configuration that permits the reading of measurement data by the information acquisition device 10, it may be either a conventional measuring device or a new measuring device. In addition, the measuring device 20 may be a measuring device that permits acquisition of measurement data by the information acquisition device 10 with retrofit parts or devices, etc., and, furthermore, in such a case, it also may be either a conventional measuring device or a new measuring device. It should be noted that the phrase "configuration permitting the reading of the measurement data by the information acquisition device 10" refers, for example, to configurations permitting data communication with the information acquisition device 10.

In addition, as shown in FIG. 1, the information acquisition device 10 comprises a data acquisition unit 11, a code reading unit 12, and a data processing unit 13. In addition, the information acquisition device 10 is adapted to be able to acquire data from conventional measuring devices 20 of various types.

The data acquisition unit 11 acquires measurement data from the measuring device 20. The code reading unit 12 reads codes 31 and acquires the information 32 that is represented by the codes 31. The data processing unit 13 associates the information 32 acquired by the code reading unit 12 with the measurement data acquired by the data acquisition unit 11.

Thus, the information acquisition device 10 can associate measurement data acquired from a conventional measuring device 20 with data related to the measurement data in a simple manner. Unlike the measuring devices disclosed in Patent Documents 1 and 2 described in the Background Art section, the information acquisition device 10 does not require the measuring devices to be replaced and can use conventional measuring devices 20, thereby minimizing additional costs. In addition, the increase in the size and weight of the measuring device 20 is also minimized.

Here, the configuration of the information acquisition device 10 and measurement system 70 will be described more specifically. In Embodiment 1, the measuring device 20, which is a medical measuring device used to measure patient status, is adapted to carry out the measurement of target components in samples and accuracy testing of reference solutions used for measuring the target components with sensors.

Specifically, the measuring device 20 carries out the measurement of the target components using a sensor 24 having a sample drop 26 applied thereto. In addition, the measuring device 20 can also perform accuracy testing using a sensor 25 having a drop of a reference solution 27 applied thereto instead of the sample 26.

The term "reference solution" designates a solution used as a measurement standard to ensure the accuracy of measurement by measuring devices, for example, a solution containing a predetermined amount of a target component. Accordingly, the accuracy of measurements performed using the measuring device can be determined by performing measurements in the measuring device 20 using the sensor 25 with a drop of a reference solution 27 and comparing the obtained measurement results with pre-configured conditions (preset conditions).

Specifically, in FIG. 1, the measuring device 20 is a glucometer. In this case, blood collected from a patient is used as the sample 26. In addition, a glucose solution containing a preset amount of glucose is used as the reference solution 27. In FIG. 1, the sensor 24 and sensor 25 are identical except for the solutions applied thereto. It should be noted that in Embodiment 1, the application of the sample 26 to the sensor 24 and that of the reference solution 27 to the sensor 25 is performed after inserting the sensors 24 and 25 into the measuring device 20. However, Embodiment 1 is not limited to this implementation and an implementation may be used, in which the sensors 24 and 25 are inserted into the measuring device 20 after application.

In addition, use-by dates are usually pre-configured for the sensors and reference solutions. Accordingly, in order to obtain accurate measurement results, it is necessary to perform measurements using sensors and reference solutions that have not expired. The use-by dates will be discussed below. In FIG. 1, 21 designates a sensor insertion slot, into which the sensor 24 or 25 is inserted, and 22 designates a display screen provided in the measuring device 20.

In Embodiment 1, there are no particularly limitations as to the type of the measuring device 20. A measuring device that measures HbA1c (glycohemoglobin) by measuring liquid chromatography or HPLC etc. is suggested as another example of the measuring device 20. In addition, devices capable of measuring both blood glucose and HbA1c are also suggested. Furthermore, in addition, pedometers, weight scales, heart rate meters, body fat meters, blood pressure gauges, body height meters, seated height meters, and the like are also suggested.

In addition, in Embodiment 1, the information acquisition device 10 is further provided with a data storage unit 14 and the data processing unit 13 stores measurement data (hereinafter referred to as "associated data") having information 32 associated therewith in the data storage unit 14. Then, the data processing unit 13 transmits the associated data stored in the data storage unit 14 to a server computer 40 automatically, for example, at regular intervals, or according to operator instructions. The server computer 40 also forms part of the measurement system 70.

Furthermore, in Embodiment 1, the information acquisition device 10 also comprise a display unit 16 used for external presentation of information. The display unit 16 is made up of a display panel and circuitry that is used to control it. It should be noted that, as used herein, the term "information" refers to all information subject to external presentation. Specifically, messages, etc. presented to the operator are suggested as examples of the "information" in addition to the measurement data and information 32. In addition, the keys 1, 2, 3 and 4 in FIG. 1 indicate luminous elements, which are discussed below.

Figure 2:
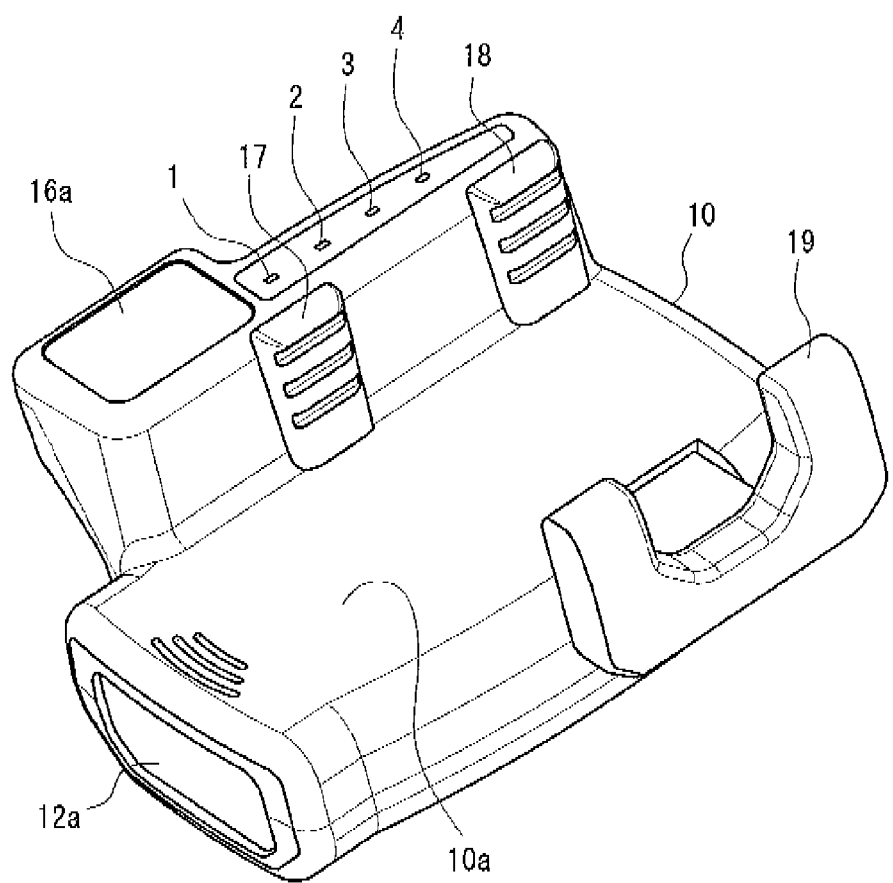
FIG. 2 is an oblique view illustrating the appearance of the information acquisition device used in Embodiment 1 of the present invention.
Figure 3:
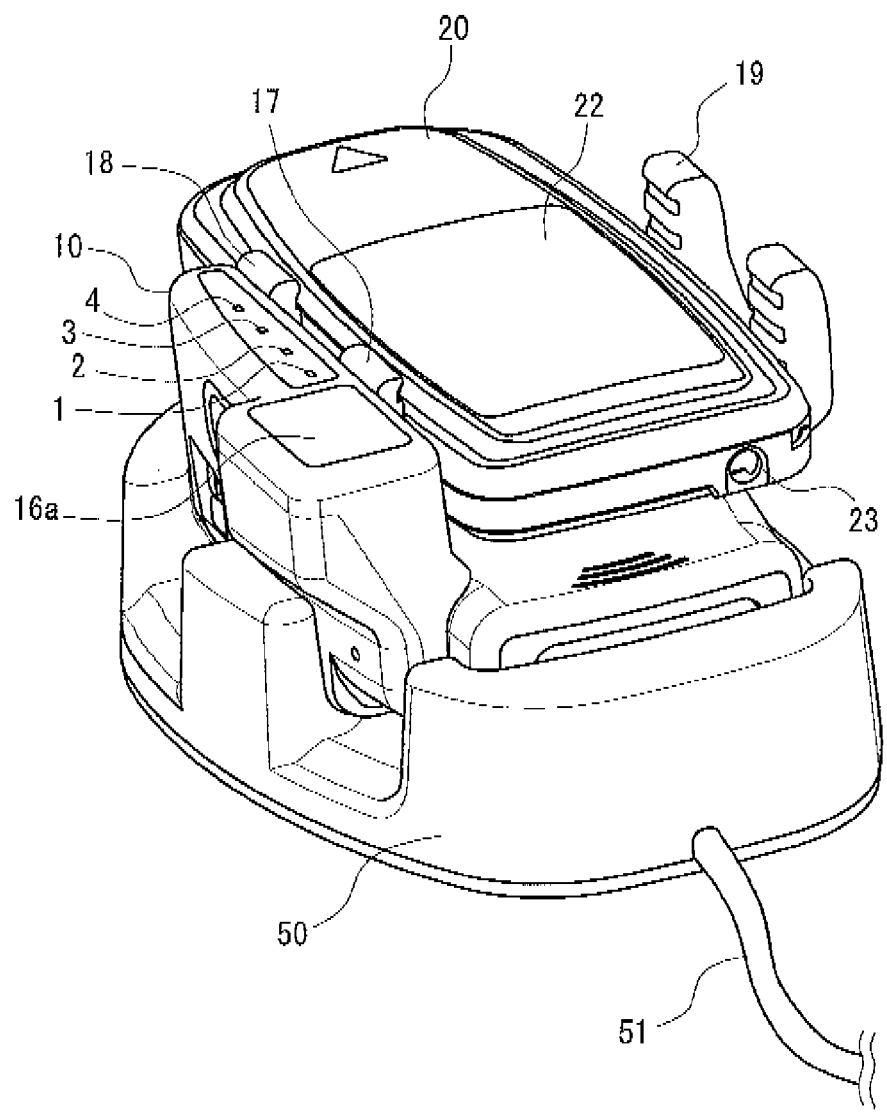
FIG. 3 is an oblique view illustrating the information acquisition apparatus depicted in FIG. 2 with a measuring device and a docking station connected thereto.

Here, the external appearance of the information acquisition device 10 and measurement system 70 will be described with reference to FIG. 2 and FIG. 3. FIG. 2 is an oblique view illustrating the appearance of the information acquisition device used in Embodiment 1 of the present invention. FIG. 3 is an oblique view illustrating the information acquisition apparatus depicted in FIG. 2 with a measuring device and a docking station connected thereto.

As shown in FIG. 2 and FIG. 3, the information acquisition device 10 is configured such that the measuring device 20 can be mounted on a mounting surface 10a. The measuring device 20 is held on the mounting surface 10a clamped by clamping members 17 and 18 and a clamping member 19, which is disposed in a face-to-face relationship thereto. In addition, the information acquisition device 10 and measuring device 20 are connected by a communication cable, not shown in FIG. 2 or FIG. 3, and the information acquisition device 10 acquires measurement data through the communication cable.

It should be noted that in Embodiment 1, there are no particular limitations as to the implementation of connection between the information acquisition device 10 and measuring device 20, which can also be effected using wireless communication.

In addition, in FIG. 2, 16a designates a display screen and 12a designates a code reading surface of the code reading unit 12. In FIG. 3, 23 designates a plug-in opening for the communication cable.

In addition, as shown in FIG. 2, the information acquisition device 10 comprises multiple luminous elements 1-4 in the vicinity of the display screen 16a. In Embodiment 1, light-emitting diodes are used as the luminous elements. These luminous elements 1-4 may emit either the same color or mutually different colors.

In addition, in Embodiment 1, the respective illumination, flashing, and extinguishing of the luminous elements 1-4 is carried out by the data processing unit 13 (see FIG. 1) in response to predetermined operations performed by the operator. The data processing unit 13 uses the respective illumination, flashing, and extinguishing of the luminous elements 1-4 to confirm the completion of operations, for notifying the operator of errors and problems related to the information acquisition device 10 or sensors, as well as for notifying the operator of the charge state of the information acquisition device.

Specifically, prior to or subsequent to the completion of a predetermined operation, the data processing unit 13 notifies the operator of the safe completion of the operation by changing the emissive state of a luminous element from flashing to steady illumination. In addition, if a problem or error occurs in the information acquisition device 10 or sensor, the data processing unit 13 illuminates a luminous element. Furthermore, if the information acquisition device 10 is in a charged state, the data processing unit 13 steadily illuminates a luminous element, and if its charge is below a threshold value, changes the emissive state of said luminous element from steady illumination to flashing.

For example, suppose the luminous element 1 shown in FIG. 2 is used for error notification and charge state notification. In such a case, upon detecting a problem in the information acquisition device 10 or sensor, the data processing unit 13 steadily illuminates the currently extinguished luminous element 1.

In addition, suppose the luminous element 2 is used for the confirmation of completion of reading of a measurement operator ID (see FIG. 4 (a)), the luminous element 3 is used for the confirmation of completion of reading of a patient ID, and the luminous element 4 is used for the confirmation of completion of measurement data reception.

In such a case, if the code reading unit 12 is waiting for the completion of reading of a measurement operator ID, the data processing unit 13 flashes the luminous element 2. Then, upon correct completion of the operation of reading of the measurement operator ID in the code reading unit 12 (see FIG. 1) in this state, the data processing unit 13 steadily illuminates the luminous element light 2.

In addition, when the code reading unit 12 is waiting for the completion of reading of a patient ID, the data processing unit 13 flashes the luminous element 3. Then, upon correct completion of the operation of reading of the patient ID in the code reading unit 12 in this state, the data processing unit 13 steadily illuminates the luminous element light 3.

After that, if the data acquisition unit 11 is waiting for the completion of measurement data acquisition, the data processing unit 13 flashes the luminous element 4. Upon correct completion of the operation of measurement data acquisition in the data acquisition unit 11 in this state, the data processing unit 13 steadily illuminates the luminous element light 4.

Thus, if the data processing unit 13 carries out the steady illumination, flashing and extinguishing of the luminous elements 1-4 in response to predetermined operations performed by the operator, the operator can confirm whether or not the operations have correctly completed in a simple manner. It should be noted that the correspondence between the luminous elements and their intended purpose may be rendered either fixed or variable by rewriting the software.

Furthermore, although the information acquisition device 10 displays the requisite information on the display screen 16a in response to various operations etc., the size of the display screen 16a is limited, and information that cannot be displayed in its entirety can be displayed by scrolling in the vertical or horizontal direction of the display screen 16a.

In addition, if the information acquisition device 10 has a built-in acceleration sensor, it can detect its own orientation and can adjust the orientation of the information displayed on the display screen 16a in accordance with the detected orientation. This is convenient because the information can be read correctly no matter how the operator holds the information acquisition device 10.

In addition, this is convenient because if information can be displayed by changing the orientation in this manner, then the orientation of display on the display unit 16 of the information reading device 10 can be made to coincide with the orientation of display of measurements in the measuring devices 20 when the directions of measurement display on the display screens of multiple measuring devices are different.

In addition, in order to enable the above-described display, a table that associates identification information used for identifying each measuring device with information regarding the orientation of data display in each measuring device is stored in the data storage unit 14 (see FIG. 1) of the information reading device 10. On the other hand, the measuring device 20 has to be provided with functionality for outputting the identification information used to identify said measuring device 20 wirelessly or by wire.

In Embodiment 1, the transmission of the identification information from the measuring device 20 can be effected if the measuring device 20 outputs measurement data along with identification information attached thereto. Specifically, in the example of FIG. 3, the measuring device 20 and information reading device 10 are electrically connected by inserting the communication cable provided in the information reading device 10 into the plug-in opening 23 of the measuring device 20, thereby enabling data communication therebetween. In this state, the identification information that identifies said measuring device 20 is then transmitted from the measuring device 20 to the information reading device 10 along with the measurement data.

Subsequently, upon acquisition of the identification information along with the acquired data, the data acquisition unit 11 (see FIG. 1) supplies them to the data processing unit 13 (see FIG. 1). Upon receiving the identification information, the data processing unit 13 refers to the table stored in the data storage unit 14 and identifies the orientation of display corresponding to the received identification information. Then, when the data processing unit 13 provides the display unit 16 with instructions regarding the identified orientation, the display unit 16 displays the data on the display screen 16a in the identified orientation. The display unit displays the data in the specified orientation.

Furthermore, as shown in FIG. 3, in Embodiment 1, a docking station 50 is employed in order to facilitate connection between the information acquisition device 10 and the server computer 40. The docking station 50 is connected to the server computer 40 through a communication cable 51. In addition, the docking station 50 is provided with a connector (not shown in FIG. 3) that can be connected to the communication interface of the information acquisition device 10 in a simple manner. Accordingly, by installing the information acquisition device 10 in the docking station 50, the operator can connect the information acquisition device 10 to the server computer 40 and transfer the information stored in the information acquisition device 10 to the server computer 40.

In addition, the docking station 50 can operate as a charger supplying electrical power to the information acquisition device 10. Furthermore, if the docking station 50 is operated as a charger, then, in a preferred implementation, the docking station 50 determines the remaining capacity of the battery of the information acquisition device 10 and initiates charging when the remaining capacity is below a threshold value.

The codes subject to reading in Embodiment 1 will be described next. In Embodiment 1, the codes to be read by the code reading unit 12 are, for example, one-dimensional codes represented by barcodes and two-dimensional codes represented by QR codes.

A code reading unit capable of reading codes displayed on a display screen or media such as paper and the like is suggested as the code reading unit 12 in Embodiment 1. In addition, there are no particular limitations as to the code reading system, which can be, for example, an optical system. In the example of FIG. 1, barcodes are used as the codes 31 and a barcode reader unit is used as the code reading unit 12.

In addition, in Embodiment 1, information managed by medical personnel at a hospital, which is shown, for example, in FIGS. 4 (a) and (b), is suggested as the information represented by the codes, i.e. as the information associated with the measurement data (information 32 illustrated in FIG. 1). Furthermore, in Embodiment 1, as described below, the information acquisition device 10 can operate in a quality control mode intended to avoid faulty measurement results and, in such a case, codes representing information illustrated in FIG. 4 (c) are also employed in the execution of the quality control mode. In addition, the codes illustrated in FIG. 4 (a)-(c) may be either printed on sheet-like media such as paper, etc., or displayed on a display screen.

Below, the codes will be specifically described with reference to FIG. 4 (a)-(c). FIGS. 4 (a)-(c) are diagrams illustrating exemplary codes used in Embodiment 1 of the present invention. In addition, although in the example of FIG. 4 (a)-(c) the codes are barcodes, the gist of Embodiment 1 is not limited thereto.

FIG. 4 (a) illustrates codes that represent identification information. The identification information is information used to identify the origin of the measurement data. In FIG. 4 (a), information that identifies patients (patient IDs) and information that identifies operators performing measurements (measurement operator IDs) is shown as an example of the identification information.

In addition, FIG. 4 (b) illustrates codes that represent health information. In this embodiment, the measurement data is associated not only with identification information, but also with health information. The term health information refers to all the information related to the health of the patients subject to measurements. As shown in FIG. 4 (b), information representing bodily features, such as "body weight" and "body height", as well as information such as "preprandial" and "postprandial", which indicates the status of the patient at the time when the measurement data is obtained, is suggested as specific examples. In addition, among these health information items, "preprandial" and "postprandial" are made up of parameters only, while "body weight" and "body height" are made up of parameters and numerical values. When the latter are read, the operator first reads the barcodes of the parameters and then reads the barcodes of the corresponding numerical values.

In addition, FIG. 4 (c) illustrates codes that represent use-by date information. As shown in FIG. 4 (c), in Embodiment 1, the use-by dates of the sensors (hereinafter referred to as "sensor use-by dates") and the use-by dates of the reference solutions (hereinafter referred to as "reference solution use-by dates") are suggested as the use-by date information. The barcodes that represent sensor use-by dates and barcodes that use reference solution use-by dates are read during the execution of the quality control mode, which is discussed below.

Figure 5:
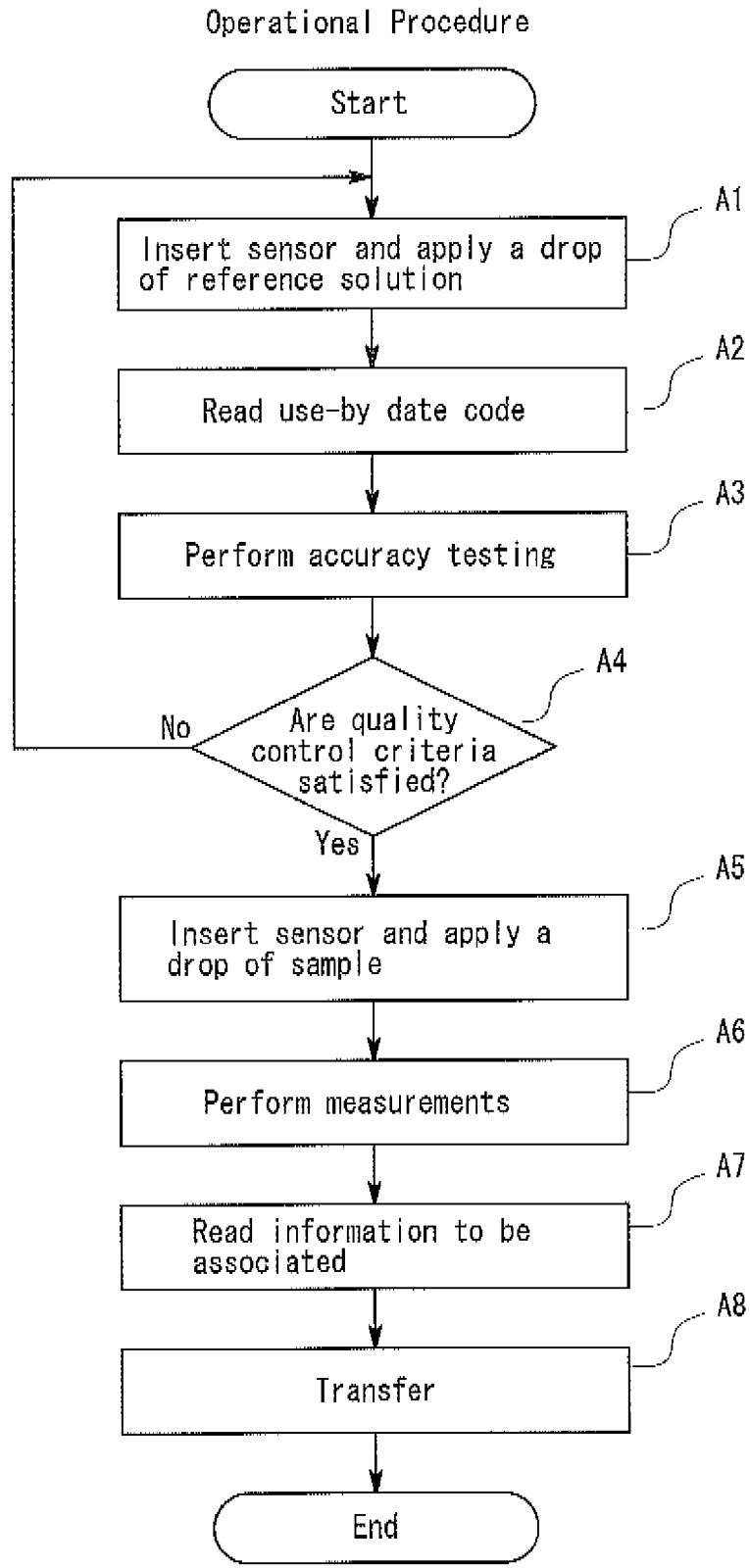
FIG. 5 is a flow chart illustrating an operational procedure performed by an operator using the information acquisition device used in Embodiment 1 of the present invention.

Next, the procedure used to operate the information acquisition device 10 will be described from an operator's standpoint with reference to FIG. 5. FIG. 5 is a flow chart illustrating an operational procedure performed by an operator using the information acquisition device used in Embodiment 1 of the present invention. In the description that follows, refer to FIG. 1-FIG. 4 as appropriate.

In addition, the operator operates the information acquisition device 10 by switching between the operational modes of the device. In Embodiment 1, operational modes configurable in the information acquisition device 10 include two modes, namely, the above-described quality control mode and the measurement mode. The measurement mode is a mode used to carry out the association of information with the measurement data.

First of all, the operator sets the operational mode of the information acquisition device 10 to the quality control mode. Then, as shown in FIG. 5, the operator inserts a sensor 25 into the sensor insertion slot 21 of the measuring device 20 and applies a drop of a reference solution 27 to the distal end of the sensor 25 (Step A1). In addition, prior to, or subsequent to, the execution of Step A1, the operator places a measuring device 20 in the information acquisition device 10 and then insert a communication cable (not shown) provided in the information acquisition apparatus 10 into the plug-in opening 23, thereby electrically connecting the measuring device 20 to the information acquisition device 10 (see FIG. 3).

Next, the operator turns the code reading surface 12a of the information acquisition device 10 to codes representing sensor use-by dates and codes representing reference solution use-by dates, thereby reading them (Step A2).

Next, the operator performs accuracy testing by operating the measuring device 20 (Step A3). Upon execution of the operator's operations of Steps A1-A3, the information acquisition device 10 makes a determination as to whether or not quality control criteria are satisfied, as illustrated in the hereinafter described FIG. 6. The information acquisition device 10 then displays the results of the determination on the display screen 16a (see FIG. 2). It should be noted that the operation of the information acquisition device 10 in the quality control mode is described below with reference to FIG. 6.

In addition, in Embodiment 1, due to the fact that the operational mode is set by the operator in this manner, the information acquisition device 10 is preferably configured to permit operational mode switching in a simple manner (for example, using a mode changeover switch). Furthermore, it is particularly preferable for the information acquisition device 10 to be configured to accept the operations of the Steps A1-A3 performed by the operator only if the operator has set the operational mode to the quality control mode. As a result, if the quality control mode has not been configured, the information acquisition device 10 will only accept operations in the measurement mode, which is shown below.

Furthermore, in Embodiment 1, there are no particular limitations as to the order of execution of the above-described Steps A1-A3. Namely, for example, after reading a code representing a sensor use-by date and then reading a code representing a reference solution use-by date, the operator inserts a sensor 25 in the measuring device 20 and applies a drop of a reference solution 27 thereto. In addition, in this case, as shown in the hereinafter described FIG. 6, the information acquisition device 10 acquires the measurement data of the reference solution and then makes a determination as to whether or not the quality control criteria are satisfied.

Next, the operator checks the display screen 16a to confirm whether or not the quality control criteria are satisfied (Step A4). If it is determined as a result of Step A4 that the quality control criteria are not satisfied, the operator carries out Step A1 once again using a new sensor 25 and the reference solution.

In Embodiment 1, if it is determined in Step A4 that, for example, the use-by date of the sensor, or that of the reference solution, or both has expired, the information acquisition device 10 displays a message to that effect on the display screen 16a of the display unit 16 (see FIG. 2). In addition, when the reference solution is not within the predetermined concentration range, the information acquisition device 10 can display a message to that effect on the display screen 16a of the display unit 16. In addition, in Embodiment 1, as described below, when the quality control criteria are not satisfied, the information acquisition device 10 may emit an auditory or optical alert to notify the operator of the fact. In such a case, based on the alert, the operator determines that the quality control criteria are not satisfied.

On the other hand, if it is determined as a result of Step A4 that the quality control criteria are satisfied, the operator removes the sensor 25 and inserts a new sensor 24 in the insertion slot 21 of the measuring device 20 and applies a drop of the sample 26 thereto (Step A5). In addition, in Step A5, the operator sets the operational mode of the information acquisition device 10 to the measurement mode. The operator then measures the target component by operating the measuring device 20 (Step A6).

When the operator, as described above, sets the operational mode of the information acquisition device 10 to the measurement mode, the information acquisition device 10 enters a state, in which it cannot accept the operations illustrated in Steps A1-A3. The information acquisition device 10 then enters a state, in which it can only accept operations subsequent to Step A5.

Subsequently, the operator turns the code reading surface 12a of the information acquisition device 10 to the codes illustrated in FIGS. 4 (a) and (b), thereby reading the information to be associated (Step A7). In Embodiment 1, the operator reads codes that represent, for example, patient IDs, measurement operator IDs, "preprandial" or "postprandial, as well as "body weight", "body weight" values, "body height" and "body height" values.

It should be noted that although Step A7 is executed subsequent to Steps A1-A6 in FIG. 5, Embodiment 1 is not limited to such an arrangement, and Step A7 may be carried out at any stage, as long as it is between the start (Start) of operation and the beginning of the transfer operation (the hereinafter described Step A8). For example, Step A7 may be carried out before Steps A1-A3. In addition, Step A5 and Step A6 may be carried out after carrying out Step A7. Furthermore, Embodiment 1 may be implemented such that Step A7 is carried out after executing Step A5, with Step A6 carried out after that.

When the execution of Steps A5-A7 is complete, the information acquisition device 10 associates the measurement data with the information. As a result, the associated data is stored in the data storage unit 14 of the information acquisition device 10. It should be noted that the operation of the information acquisition device 10 in the measurement mode is described below with reference to FIG. 7.

After that, the operator attaches the information acquisition device 10 to the docking station 50 and transfers the associated data stored in the data storage unit 14 (Step A8). As a result of executing Step A8, the information acquisition device 10 is connected to the server computer 40 and transfers the associated data stored in the data storage unit 14 to the server computer 40.

After the operator executes of the operations set forth in the above-described Steps A1-A8, the measurement data acquired by the measuring device 20 is associated with the relevant data and then automatically sent to the server computer 40, where it is managed. In addition, if at this point the operator replaces the measuring device 20 connected to the information acquisition device 10 with a measuring device 20 from another patient and carries out Steps A1-A8, the measurement data of the other patient is also associated with the relevant data and then sent to the server computer 40.

Next, the operation of the information acquisition device 10 will be explained with reference to FIG. 6 and FIG. 7. As described above, the information acquisition device 10 can operate in two operational modes, i.e. in the quality control mode and in the measurement mode.

Figure 6:
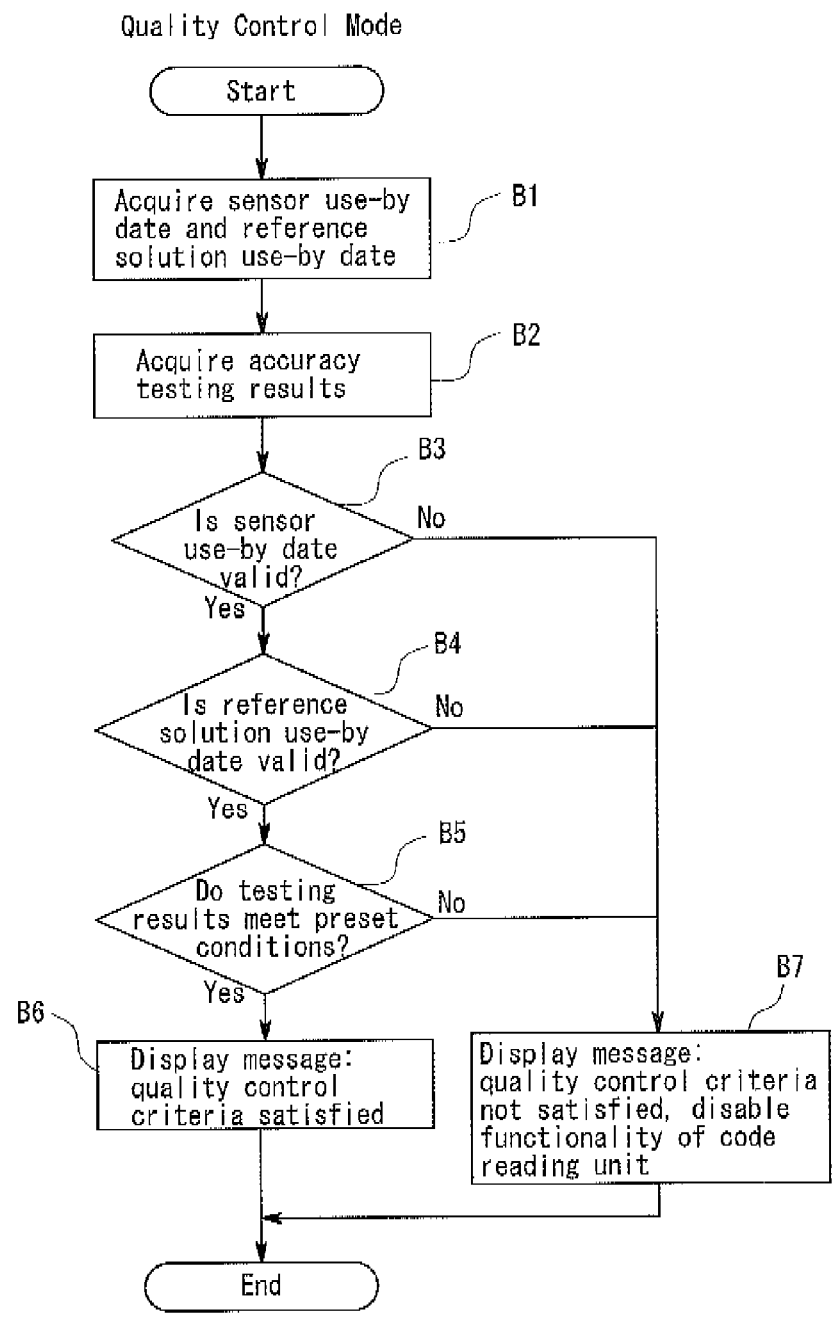
FIG. 6 is a flow chart illustrating the operation of the information acquisition device used in Embodiment 1 of the present invention in the quality control mode.

FIG. 6 is a flow chart illustrating the operation of the information acquisition device used in Embodiment 1 of the present invention in the quality control mode. FIG. 7 is a flow chart illustrating the operation of the information acquisition device used in Embodiment 1 of the present invention in the measurement mode. It should be noted that the description of the information acquisition method of Embodiment 1 is replaced by the following description of the operation of the information acquisition device 10. Furthermore, in the description that follows, refer to FIG. 1-FIG. 4 as appropriate.

As shown below, in Embodiment 1, the data processing unit 13 determines whether or not at least one of the sensor use-by date and reference solution use-by date acquired by the code reading unit 12 has expired only when operating in the quality control mode. Furthermore, in Embodiment 1, the data processing unit 13 also determines whether or not the reference solution-related measurement data (accuracy testing results) meets the preset conditions. Specifically, suggested preset conditions include, among others, the target component being within a predetermined concentration range, the concentration value of the target component being the correct concentration value, etc.

In addition, as mentioned above, the data processing unit 13 (information acquisition device 10) associates the information 32 with the measurement data only when operating in the measurement mode. For example, if the information acquisition device 10 is implemented on a computer, as described below, such mode switching can be implemented using a software program installed on the computer.

(Quality Control Mode)

At first, the quality control mode will be described with reference to FIG. 6. First of all, as shown in FIG. 6, when the operator sets the operational mode of the information acquisition device 10 to the quality control mode and carries out the operations of Steps A1-A3 illustrated in FIG. 5, the data processing unit 13 acquires the sensor use-by date and the reference solution use-by date (see FIG. 4 (*c*)) from the code reading unit 12 (Step B1). Subsequently, the data processing unit 13 acquires the accuracy testing results from the data acquisition unit 11 (Step B2).

Next, the data processing unit 13 determines whether or not the sensor use-by date has expired (Step B3). Specifically, the data processing unit 13 compares the sensor use-by date acquired in Step B1 and the current date and time to determine whether or not the current date and time is within the sensor use-by period. If the result of the determination made in Step B3 indicates that it has expired, the data processing unit 13 carries out Step B7. Step B7 is described below.

On the other hand, if the result of the determination made in Step B3 indicates that it is still valid, the data processing unit 13 determines whether or not the reference solution use-by date is still valid (Step B4). Specifically, the data processing unit 13 compares the reference solution use-by date acquired in Step B1 and the current date and time to determine whether or not the current date and time is within the reference solution use-by period. If the result of the determination made in Step B4 shows that it has expired, the data processing unit 13 carries out Step B7.

It should be noted that it is sufficient to set up the order of steps from Step B1 to Step B5, which is described below, such that Steps B3 and B4 are carried out after Step B1 and Step B5 is carried out after Step B2, and it is possible to change the order as long as these conditions are satisfied. For example, after carrying out Step B1, Step B3, and Step B4, the data processing unit 13 can carry out Step B2 and then Step B5. Alternatively, Step B4 may be carried out after executing Step B1, and Step B3 may be performed thereafter.

In addition, if the result of the determination made in Step B4 indicates that it is still valid, the data processing unit 13 determines whether or not the accuracy testing results obtained in Step B2 meet the preset conditions (Step B5). If the result of the determination made in Step B5 indicates that the accuracy testing results do not meet the preset conditions, the data processing unit 13 carries out Step B7.

Since the measuring device 20 in Embodiment 1 is a glucometer, conditions such as the blood glucose value being within a predetermined concentration range, the blood glucose concentration value corresponding to an appropriate value, etc. are suggested as the preset conditions. This predetermined concentration range is set as appropriate in accordance with the specifications of the reference solution.

On the other hand, if the result of the determination made in Step B5 indicates that the results of accuracy testing meet the preset conditions, the data processing unit 13 determines that the quality control criteria have been met and displays a message to the effect that the quality control criteria have been met on the display screen 16*a* (see FIG. 2) (Step B6). In addition, in Step B6, in addition to displaying a message to the effect that the quality control criteria have been met, or instead of that, the data processing unit 13 can also exercise control such that processing of the measurement data (measurement data obtained from the sensor 24) describing the sample 26 is performed in the information acquisition device 10. In such an implementation, the information acquisition device 10 processes measurement data describing the sample 26 only if the quality control criteria have been met. As a result, the poor quality of the measurement results is reliably minimized.

Here, the phrase "processing of the measurement data describing the sample 26" implies that measurements are carried out with the sensor 24 and the measurement data that describes the sample 26 is subjected to processing using the data acquisition unit 11, the code reading unit 12, and the data processing unit 13. In addition, the term "control intended to ensure that processing is performed in the information acquisition device 10" refers, for example, to control intended to cause the data acquisition unit 11 to acquire measurement data from the external measuring device 20; control intended to cause the code reading unit 12 to read the codes; control intended to ensure that the data processing unit 13 itself performs the association of information; or control that combines two or more of the above-mentioned types of control, etc.

In addition, if the data processing unit 13 determines in Step B7 that the quality control criteria have not been met, a message to the effect that the quality control criteria have not been met is displayed on the display screen 16*a* of the display unit 16 (see FIG. 2). In addition, as far as the data processing unit 13 is concerned, in addition to such processing, or instead of such processing, the data processing unit 13 can exercise control intended to ensure that no processing of the measurement data describing the sample 26 is performed in the information acquisition device 10. In Embodiment 1, the phrase "control intended to ensure that no processing of the measurement data describing the sample 26 is performed in the information acquisition device 10" refers to control intended to ensure that the measurement mode of the information acquisition device 10 is not executed.

In Embodiment 1, the term "control intended to ensure that the measurement mode of the information acquisition device 10 is not executed" refers to control intended to ensure that no acquisition of measurement data from the external measuring device 20 is performed by the data acquisition unit 11; control intended to ensure that no reading of codes by the code reading unit 12 is allowed; control intended to ensure that the data processing unit 13 itself does not perform association of information; or control that combines two or more of the above-mentioned types of control, etc. Specifically, if the data processing unit 13 directs the code reading unit 12 to cease operation, then, as a result, the Step A7 illustrated in FIG. 5 is not executed and, consequently, the operator can no longer perform measurements and a situation producing faulty measurement results is avoided.

Furthermore, although messages to the effect that the quality control criteria have been met and to the effect that the quality control criteria have not been met are outwardly communicated in Embodiment 1 by displaying them on the display unit, the outbound notifications are not limited to such implementations and may also be carried out using sounds, flashing lights, and the like. In particular, when communicating a message to the effect that the quality control criteria have not been met, it is preferable to perform outbound notification in the form of an alert.

In addition, in Embodiment 1, after the execution of Steps B6 and B7, the data processing unit 13 can identify, for example, the time that has elapsed after determining that the quality control criteria have been met and the number of times the measuring device 20 has carried out accuracy testing and can store the identified values in the data storage unit 14. In such a case, the information acquisition device 10 preferably determines the period required for accuracy testing based on the time elapsed after the previous accuracy testing and the number of times accuracy testing has been carried out and communicates the resultant period to the operator in the form of a message. In such an implementation, the accuracy of measurement is maintained and it becomes easy to obtain correct measurement results. Furthermore, as described below, if there are multiple measuring devices 20 corresponding to a single information acquisition device 10, the data processing unit 13 saves the elapsed times and frequencies for each of the measurement devices.

In Embodiment 1, the information acquisition device 10 may be configured such that the operator does not set up the quality control mode and the measurement mode can be executed even without executing the operations of Steps A1-A3 (see FIG. 5). In other words, the information acquisition device 10 may be configured such that the measurement mode can be executed even without carrying out the above-described Step B2, Step B3, and Step B4.

If such a configuration is used, then, if the operator performs the operation of Step A1 and the measuring device 20 acquires measurement data describing the reference solution 27, the data processing unit 13 of the information acquisition device 10 can acquire measurement data describing the above-mentioned reference solution from the data acquisition unit 11. In this case the measurement data describing the reference solution is then stored in the data storage unit 14. Subsequently, when the operator carries out Step A5, the measurement data describing the reference solution has already been stored in the data storage unit 14, as a result of which the data processing unit 13 assumes that accuracy testing has already been completed and enables the execution of the subsequent operations.

Thus, the implementation, in which Steps B2-B4 are not carried out, is useful, for example, if the operator determines whether or not the quality control criteria have been met by personally visually confirming the suitability of the measurement values obtained as a result of accuracy testing and use-by date information displayed on the packaging etc. of the sensors and reference solutions. In addition, if the information acquisition device 10 is implemented on a computer, the above-described configuration can be implemented using a software program installed on the computer.

(Measurement Mode)

Next, the measurement mode will be described with reference to FIG. 7. First of all, as shown in FIG. 7, when the operator performs Steps A5-A7 illustrated in FIG. 5, the data processing unit 13 acquires the measurement data of the measuring device 20 from the data acquisition unit 11 (Step C1) and acquires the information read from the code reading unit 12 (Step C2).

Next, the data processing unit 13 associates the information acquired in Step C2 with the measurement data acquired in Step C1. If the information acquired in Step C2 is made up of multiple items, in Step C3, the acquired multiple information items are associated with the measurement data.

In addition, in Embodiment 1, multiple barcodes can be used as the codes. In this case, for example, as shown in FIG. 4 (a)-(c), the number of digits in each barcode can be pre-defined in accordance with the type of information represented by the barcode. This also makes it possible to pre-configure the order, in which the barcodes are read. However, there are no particular limitations as to whether this order should be set in advance or not.

Furthermore, if the number of digits in each barcode is predefined in accordance with the type of information, in Step C3, the data processing unit 13 may identify the number of digits in each barcode read by the code reading unit 12 in the order, in which they are read, and determine whether or not the identified order is a pre-configured order. At such time, the data processing unit 13 may associate information with the measurement data only if the reading order is the pre-configured order. When such an implementation is used, the management of information in the data storage unit 14 is facilitated because the data processing unit 13 can identify the type of information from the reading order. It should be noted that Embodiment 1 is not limited to such an implementation.

Next, the data processing unit 13 stores the associated data obtained by association in Step C3 in the data storage unit 14 (Step C4).

Incidentally, it is assumed that the operator has not performed the reading operation of Step A7 and has not read the information to be associated. In this case, in Step C3, the data processing unit 13 can associate dummy data with the measurement data acquired in Step C1. Such processing by the data processing unit 13 makes it possible to avoid loss of measurement data due to the absence of information to be associated. In addition, in this case, the data processing unit 13 can associate subsequently obtained information with the measurement data as soon as the information to be associated is obtained upon completion of the measurement mode.

Next, the data processing unit 13 determines whether or not a connection to the exterior has been established (Step C5). Specifically, the data processing unit 13 determines whether or not the information acquisition device 10 has been attached to the docking station 50 by the operator as a result of the operation of Step A8 illustrated in FIG. 5.

If it is determined in Step C5 that a connection to the exterior has not been established, the data processing unit 13 enters a standby state. On the other hand, if it is determined in Step C5 that a connection to the exterior has been established, the data processing unit 13 transfers the associated data stored in the data storage unit 14 to the server computer 40 (Step C6). The execution of Step C6 concludes processing in the information acquisition device 10. The operator disconnects the measuring device 20 from the information acquisition device 10.

In addition, in Embodiment 1, the operator can attach another measuring device to the information acquisition device 10 and direct the information acquisition device 10 to execute Steps B1-B6 and Steps C1-C6. At such time, there are no particular limitations as to the other measuring device as long as it is suitable for use in the information acquisition device 10, and it may be a measuring device from another patient. In addition, the other measuring device may be a measuring device whose measurement principle is different from that of the initially used measuring device. In other words, the other measuring device may be a measuring device of another type used by the same patient (in addition to a glucometer, it may be, for example, a heart rate meter, a body fat meter, a blood pressure meter, etc.).

In addition, if a measuring device of another type is used by the same patient, the data processing unit 13 can use the read patient ID to retrieve previously stored measurement data that has the same patient ID associated therewith. The data processing unit 13 can then associate the newly acquired measurement data with the retrieved previous measurement data. As a result, associated data produced by associating multiple measurement data items is transferred to the server computer 40.

Figure 7:
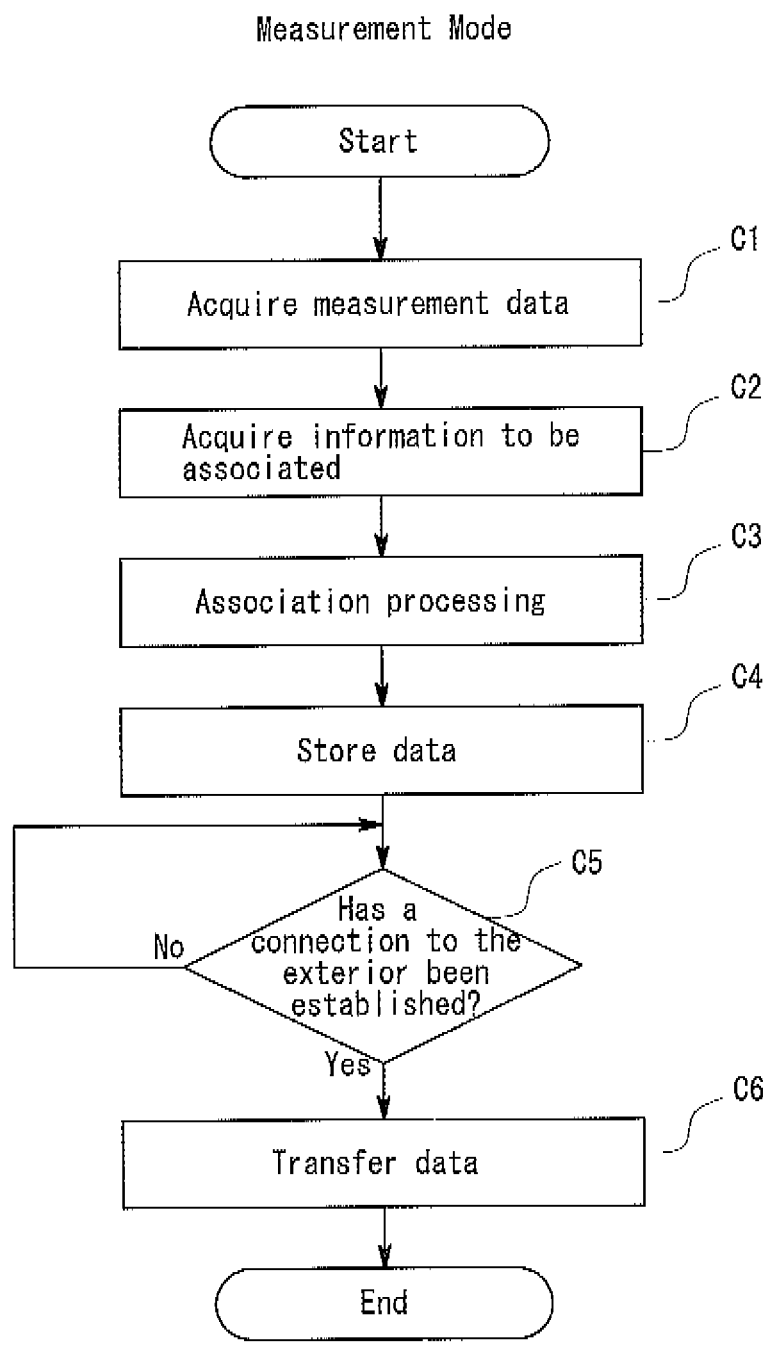
FIG. 7 is a flow chart illustrating the operation of the information acquisition device used in Embodiment 1 of the present invention in the measurement mode.

In addition, the software program used in Embodiment 1 can be any software program, as long as it causes a computer to execute Steps B1-B7 illustrated in FIG. 6 and Steps C1-C6 illustrated in FIG. 7. The information acquisition device 10 and information acquisition method used in Embodiment 1 can be implemented by installing and executing this software program on a computer. In this case, the CPU (Central Processing Unit) of the computer operates and performs processing as the data processing unit 13. In addition, an interface provided in the computer for connecting to the exterior operates as the data acquisition unit 11 and a code reading unit such as a barcode reader connected to the computer operates as the code reading unit 12. Furthermore, a hard disk drive or another storage device provided in the computer operates as the data storage unit 14.

It should be noted that the software program used in Embodiment 1 may be designed to omit some of the Steps B1-B7 and Steps C1-C6. The software program used in Embodiment 1 may be designed such that Steps C1-C6 used to execute the measurement mode can be carried out even if Step B2, Step B3, and Step B4 are not carried out, as set forth in the description of the operation of the information acquisition device 10.

As described above, in accordance with Embodiment 1, measurement data can be associated with data related thereto in a simple manner using a conventional measuring device 20. In addition, quality control for multiple measuring devices can be effected using a single information acquisition device 10, which is particularly useful in a medical institution utilizing multiple measuring devices. In addition, there are no particular limitations as to the type and number of the measuring devices that can be used in the information acquisition device 10 of Embodiment 1.

(Embodiment 2)

Figure 8:
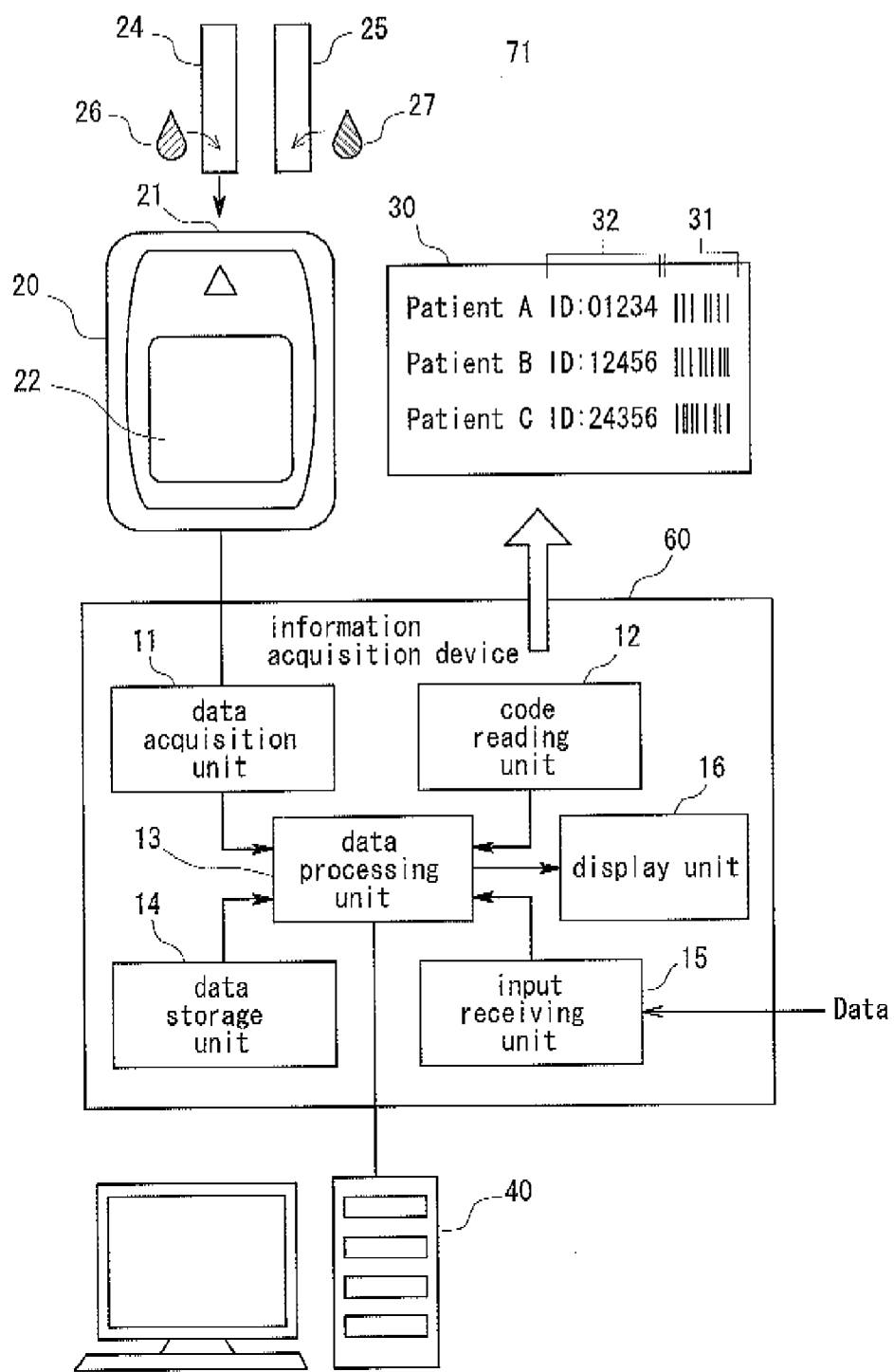
FIG. 8 is a block diagram illustrating the configuration of the information acquisition device used in Embodiment 2 of the present invention.

The information acquisition device, measurement system, information acquisition method, and software program of Embodiment 2 of the present invention will be described next with reference to FIG. 8-FIG. 10. First of all, the configuration of the information acquisition device 60 and the measurement system 71 used in Embodiment 2 will be described with reference to FIG. 8. FIG. 8 is a block diagram illustrating the configuration of the information acquisition device used in Embodiment 2 of the present invention.

As shown in FIG. 8, as an addition to the configuration of the information acquisition device 10 of Embodiment 1 illustrated in FIG. 1, the information acquisition device 60 is provided with an input receiving unit 15. The input receiving unit 15 can receive input of external information. Various implementations of input include keying and input from other devices effected wirelessly or by wire. In addition, in the information acquisition device 60, the data processing unit 13 can also associate information received by the input receiving unit 15 with measurement data.

In other words, in Embodiment 2, the information that the information acquisition device 60 can associate with the measurement data is not only the information that is read from the codes, but also the information that is inputted. In accordance with Embodiment 2, the variety of the information to be associated is increased in comparison with Embodiment 1, thereby achieving further improvement in operator convenience.

It should be noted that, except as stated above, the information acquisition device 60 is configured in the same manner as the information acquisition device 10 in Embodiment 1. Accordingly, the effects described in Embodiment 1 can also be obtained in Embodiment 2. In addition, there are no particular limitations as to the information received by the input receiving unit 15. For example, information comprising numerical values is suggested as the health information illustrated in FIG. 4 (*b*). Furthermore, except for the information acquisition device 60, the measurement system 71 is configured in the same manner as the measurement system 70 of Embodiment 1. In addition, in FIG. 8, the luminous elements 1-4 illustrated in FIG. 1 are omitted.

Next, the procedure used to operate the information acquisition device 60 will be described from an operator's standpoint with reference to FIG. 9. FIG. 9 is a flow chart illustrating an operational procedure performed by an operator using the information acquisition device used in Embodiment 2 of the present invention. In addition, refer to FIG. 8 as appropriate in the description that follows.

Figure 9:
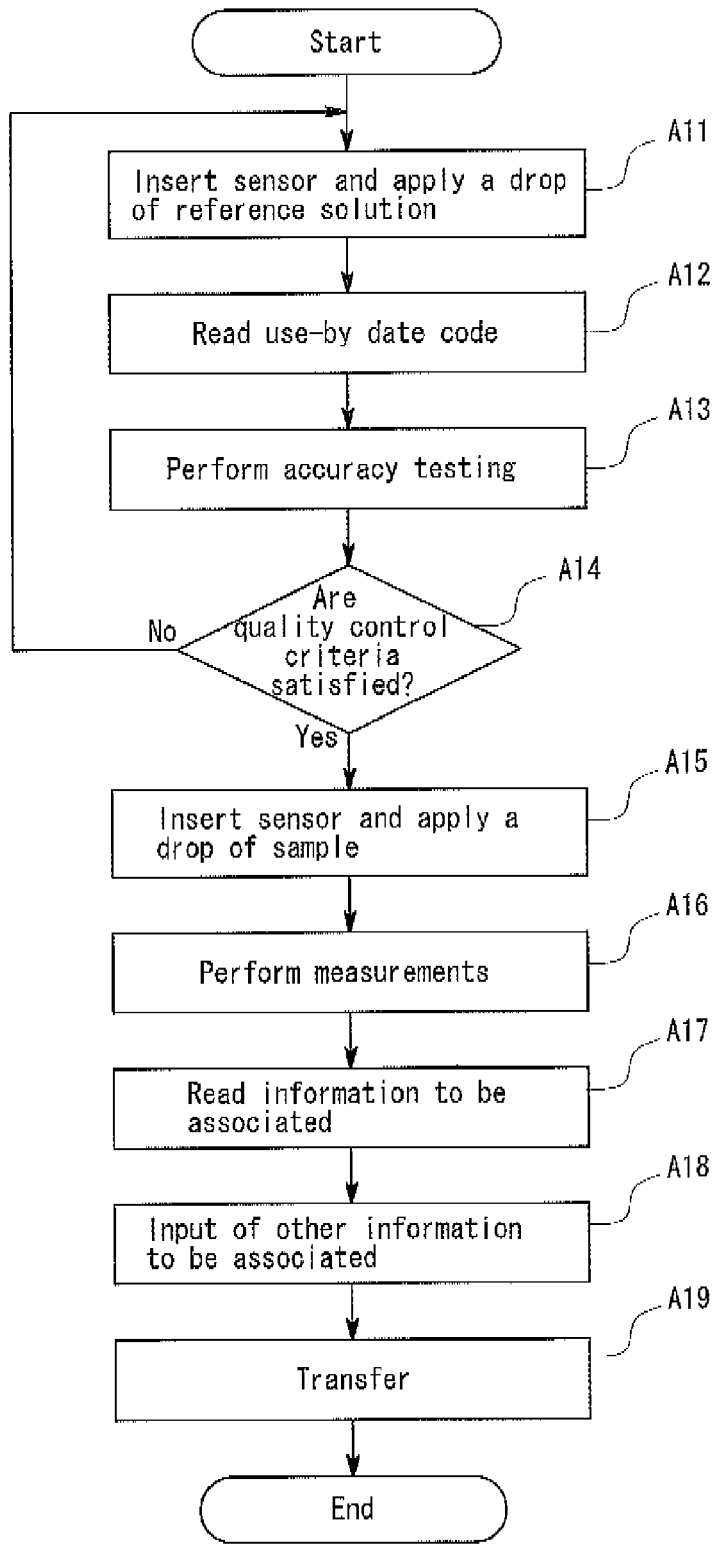
FIG. 9 is a flow chart illustrating an operational procedure performed by an operator using the information acquisition device used in Embodiment 2 of the present invention.

Among the steps illustrated in FIG. 9, Steps A11-A17 and Step A19 respectively correspond to Steps A1-A8 illustrated in FIG. 5. In contradistinction to Embodiment 1, in Embodiment 2, the operator carries out Step A18 to accept input of other information.

When Step A18 is carried out, the information acquisition device 60 operates in the measurement mode and associates the measurement data with the information acquired via reading and the information acquired via input. In addition, after carrying out Step A18, the associated data is stored in the data storage unit 14 of the information acquisition device 60.

Next, the operation of the information acquisition device 60 will be explained with reference to FIG. 10. FIG. 10 is a flow chart illustrating the operation of the information acquisition device used in Embodiment 2 of the present invention in the measurement mode. In addition, in Embodiment 2, the information acquisition method is also implemented by operating the information acquisition device 60. Accordingly, the description of the information acquisition method of Embodiment 2 is also replaced by the following description of the operation of the information acquisition device 60. It should be noted that in Embodiment 2, the information acquisition device 60 operates in the quality control mode in the same manner as the information acquisition device 10 of Embodiment 1. Accordingly, the description of its operation in the quality control mode is omitted. In addition, in the description that follows, refer to FIG. 8 and FIG. 9 as appropriate.

Figure 10:
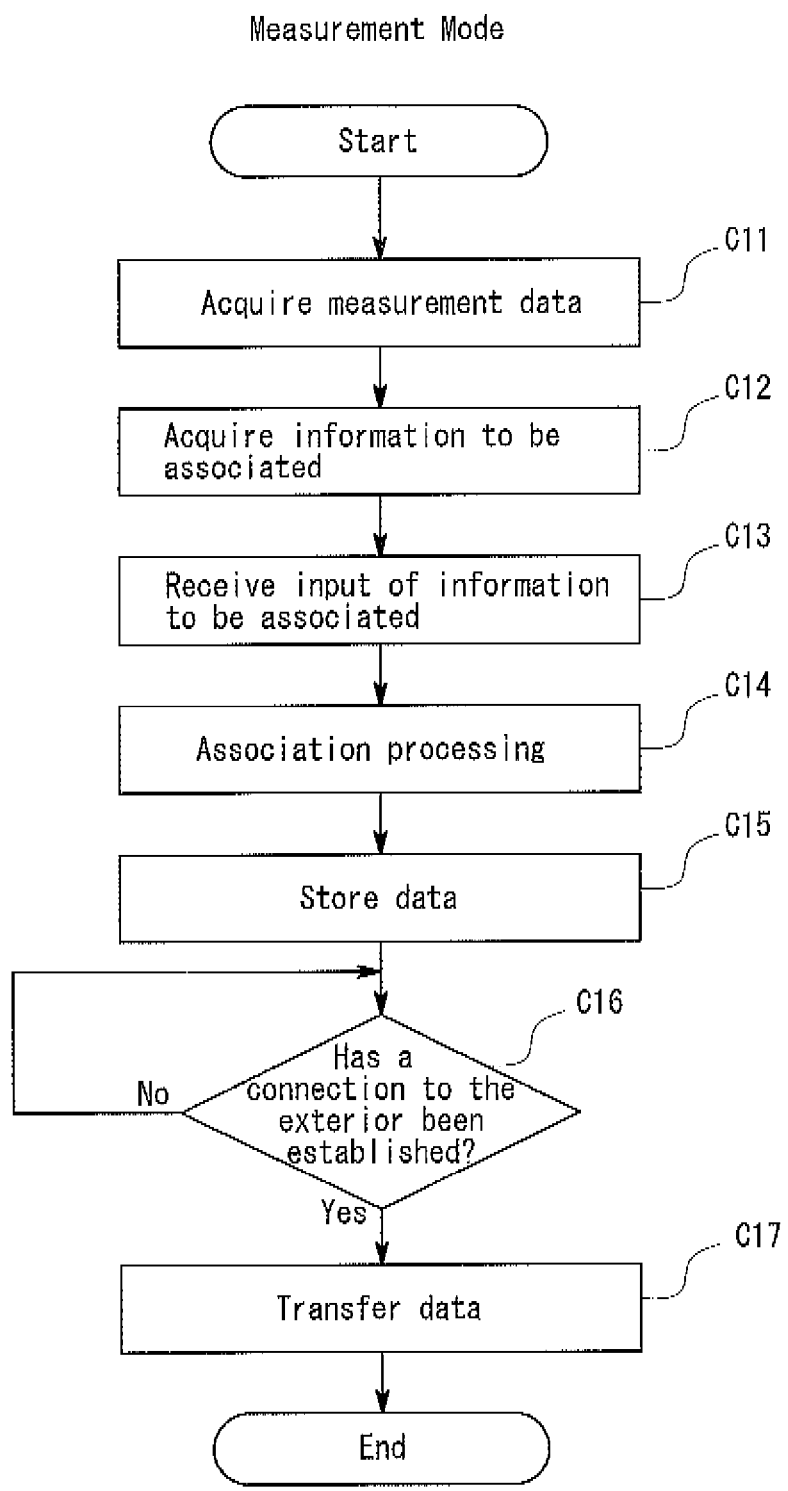
FIG. 10 is a flow chart illustrating the operation of the information acquisition device used in Embodiment 2 of the present invention in the measurement mode.

Among the steps illustrated in FIG. 10, Steps C11-C12 and Steps C15-C17 respectively correspond to Steps C1-C2 and C4-C6 illustrated in FIG. 7. In contradistinction to Embodiment 1, in Embodiment 2, upon execution of Step C12, the data input receiving unit 15 carries out Step C13 to receive input of external information. After that, in Step C14, the data processing unit 13 associates the measurement data acquired in Step C11 with the information acquired in Step C12 and information received in Step C13.

In addition, the software program used in Embodiment 2 can be any software program, as long as it causes a computer to execute Steps B1-B6 illustrated in FIG. 6 and Steps C11-C17 illustrated in FIG. 10. The information acquisition device 60 and information acquisition method used in Embodiment 2 can be implemented by installing and executing this software program on a computer. In this case, the CPU of the computer operates and performs processing as the data processing unit 13. In addition, an interface provided in the computer for connecting to the exterior operates as the data acquisition unit 11 and input receiving unit 15, and a code reading unit such as a barcode reader connected to the computer operates as the code reading unit 12. Furthermore, a hard disk drive or another storage device provided in the computer operates as the data storage unit 14.

Although in Embodiments 1 and 2 the inventive information acquisition device is used with conventional measuring devices, the present invention is not limited to this implementation. The inventive information acquisition device can be used not only with conventional measuring devices, but also with any type of measuring device configured to be used with the inventive information acquisition device.

In addition, Embodiments 1 or 2 are not limited to the above-described implementation. For example, an implementation that employs codes representing sensor identification information used for identifying sensors is suggested as another implementation. In this implementation, the code reading unit 12 acquires sensor identification information. The data processing unit 13 then determines whether or not a sensor identified by the acquired sensor identification information can be used in the measuring device 20. If the determination yields that the sensor can be used in the measuring device, the data processing unit 13 exercises control intended to ensure processing of sample-related measurement data in the information acquisition device 10 (or 60). If the sensor cannot be used in the measuring device, the data processing unit 13 exercises control intended to ensure that no processing is performed in the information acquisition device 10 (or 60), issues an outbound notification, or does both.

In addition, the data processing unit 13 exercises control intended to ensure that no processing of sample-related measurement data is performed in the information acquisition device 10 (or 60), issues an outbound notification, or does both in the following cases. Specifically, this happens if at least one of the following is true: if the code reading unit 12 cannot acquire a sensor use-by date (Step B1 of FIG. 6); if the code reading unit 12 cannot acquire a reference solution use-by date (Step B1 of FIG. 6), if the data acquisition unit 11 cannot acquire measurement data relating to the reference solution 27 (Step B1 of FIG. 6), and if the data acquisition unit 11 cannot acquire sample-related measurement data (Step C1 of FIG. 7).

(Embodiment 3)

Next, Embodiment 3 of the present invention will be explained with reference to FIG. 11 and FIG. 12. In contradistinction to Embodiments 1 and 2, in Embodiment 3, the description will focus on a measuring device, a quality control method, and a software program used to implement the same. In addition, in Embodiment 3, the main object is to avoid situations that produce faulty measurement results in the measuring device. Furthermore, in Embodiment 3, the quality control method is a method for performing quality control on sensors used in measuring devices that measure target components in samples and reference solutions used for measuring the target components.

First of all, the configuration of a measuring device 100 according to Embodiment 3 will be described with reference to FIG. 11. FIG. 11 is a block diagram illustrating the configuration of the measuring device according to Embodiment 3 of the present invention. The measuring device 100 illustrated in FIG. 11 is adapted to be able to carry out the measurement of target components in samples and accuracy testing of reference solutions used for measuring the target components with sensors. As shown in FIG. 11, the measuring device 100 can carry out the measurement of the target components using a sensor 104 having a sample drop 106 applied thereto. In addition, the measuring device 100 can also perform accuracy testing using a sensor 105 having a drop of a reference solution 107 applied thereto instead of the sample 106.

As described in Embodiment 1, the term "reference solution" designates a solution containing a predetermined amount of a target component. Accordingly, in Embodiment 3, the accuracy of measurements performed using the measuring device 100 can be determined by performing measurements in the measuring device 100 using the sensor 105 with a drop of a reference solution 107 and comparing the obtained measurement results with pre-configured conditions.

Figure 11:
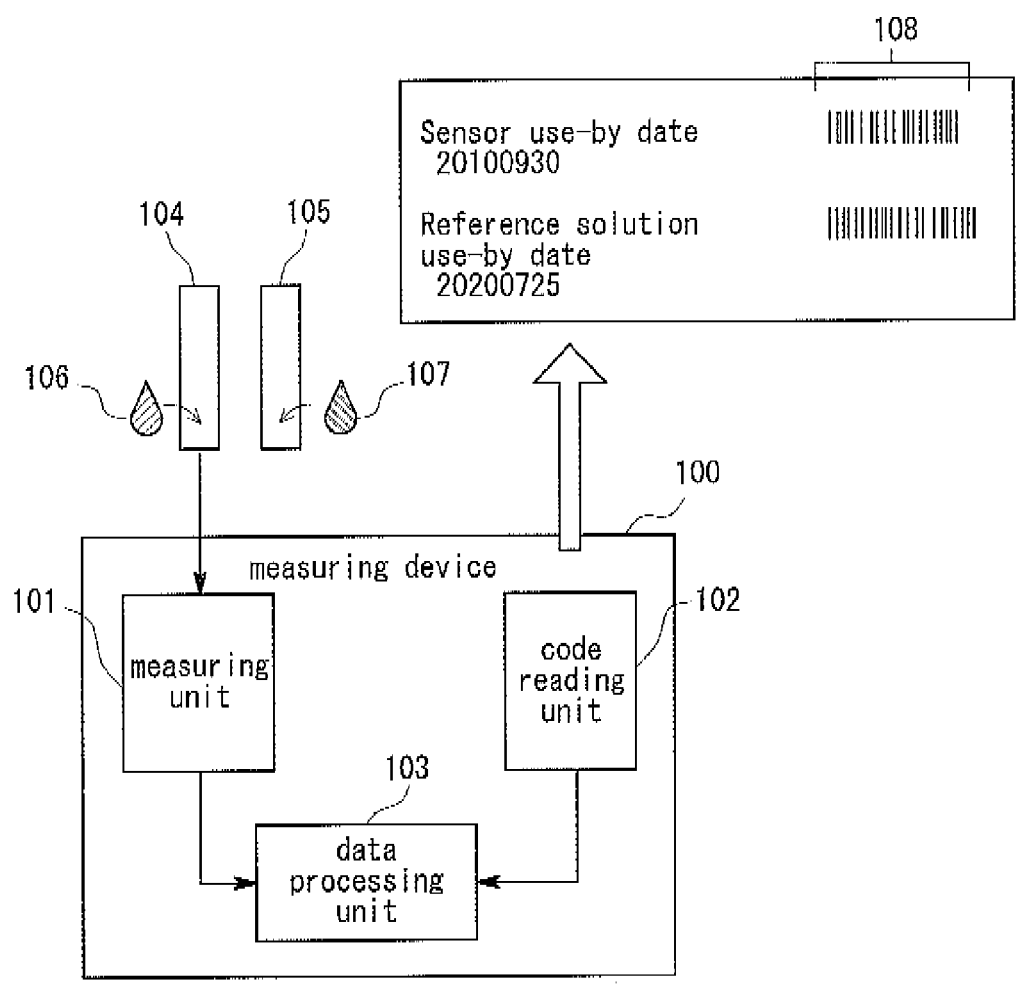
FIG. 11 is a block diagram illustrating the configuration of the measuring device according to Embodiment 3 of the present invention.

In addition, as shown in FIG. 11, the measuring device 100 comprises a measuring unit 101, a code reading unit 102, and a data processing unit 103. The measuring unit 101 performs measurements using sensors to acquire measurement data. In this embodiment, the measuring unit 101 is a medical measuring unit measuring patient status, for example, a blood glucose level measurement unit.

If a blood glucose level measurement unit is used as the measuring unit 101, blood collected from a patient is used as the sample 106. In addition, a glucose solution containing a preset amount of glucose is used as the reference solution 107. It should be noted that in FIG. 11 the sensor 104 and sensor 105 are also identical except for the solutions applied thereto.

In addition, as described in Embodiment 1, use-by dates are preset for the sensors and reference solutions used in Embodiment 3. Accordingly, in order to obtain accurate measurement results, it is necessary to perform measurements using sensors and reference solutions that have not expired. The code reading unit 102 and data processing unit 103 are provided in the measuring device 100 in order to prevent the use of expired sensors and reference solutions.

The code reading unit 102 reads a code 108 using an optical system and acquires the information represented by the code 108. In Embodiment 3, as shown in FIG. 11, codes representing use-by dates (sensor use-by dates) configured for sensors and codes representing use-by dates (reference solution use-by dates) configured for the reference solutions are used as the code 108. The code reading unit 102 reads these codes to acquire the sensor use-by dates and reference solution use-by dates.

In Embodiment 3, the codes to be read by the code reading unit 102 are one-dimensional codes represented by barcodes and two-dimensional codes represented by QR codes, etc. In addition, in the same manner as in Embodiment 1, a code reading unit capable of reading codes displayed on a display screen or media such as paper and the like is suggested as the code reading unit 102. In the example of FIG. 11, barcodes are used as the codes 108 and a barcode reader unit is used as the code reading unit 102.

The data processing unit 103 determines whether or not at least one of the sensor use-by date and reference solution use-by date acquired by the code reading unit 102 has expired. In addition, in Embodiment 3, when the measuring unit 101 performs accuracy testing and acquires measurement data at such time, the data processing unit 103 also determines whether or not the acquired measurement data meets preset conditions. It should be noted that the data processing unit 103 may be provided with only one function selected from a function used to determine whether or not at least one of the sensor use-by date and reference solution use-by date has expired, and a function used to acquire measurement data and determine whether or not it meets the preset conditions.

Suggested "preset conditions" include, among others, the target component being within a predetermined concentration range, the concentration of the target component matching the correct concentration value, etc. Furthermore, if neither the sensor use-by date nor the reference solution use-by date has expired and, at the same time, the measurement data at the time of accuracy testing meets the preset conditions, the data processing unit 103 directs the measuring unit 101 to perform measurements using the sensor 104.

Next, the operation of the measuring device 100 will be explained with reference to FIG. 12. FIG. 12 is a flow chart illustrating the operation of the measuring device used in Embodiment 3 of the present invention. In addition, in Embodiment 3, the quality control method is implemented by operating the measuring device 100. Accordingly, the description of the quality control method used in Embodiment 3 is replaced by the following description of the operation of the measuring device 100. Furthermore, in the description that follows, refer to FIG. 11 as appropriate.

Figure 12:
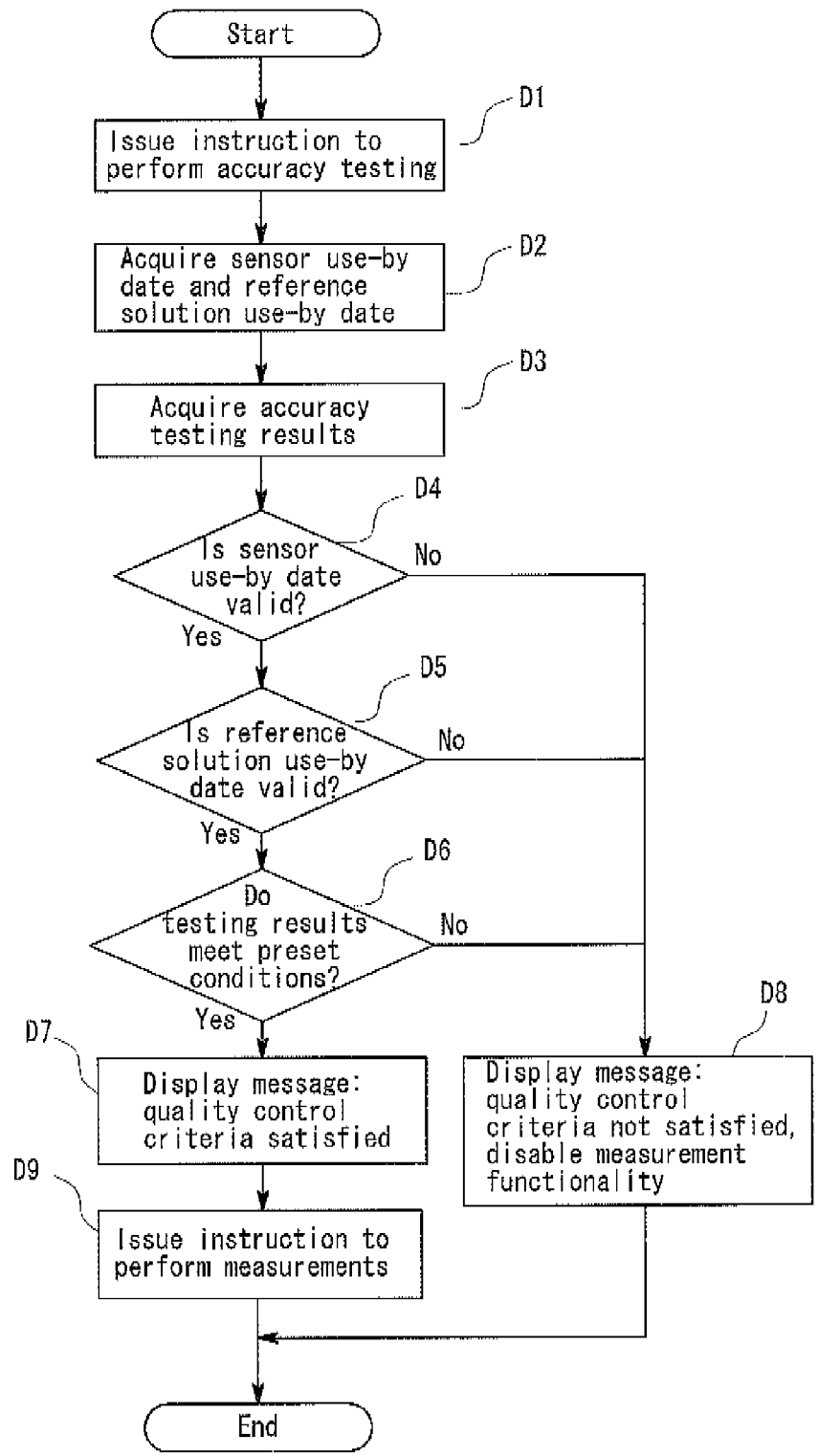
FIG. 12 is a flow chart illustrating the operation of the measuring device used in Embodiment 3 of the present invention.

First of all, as shown in FIG. 12, when the sensor 105 is placed in the measuring unit 101, the data processing unit 103 directs the measuring unit 101 to carry out accuracy testing (Step D1). Next, provided that the operator has performed the operation of code reading using the code reading unit 102, the data processing unit 103 acquires a sensor use-by date and a reference solution use-by date from the code reading unit 102 (Step D2). Subsequently, the data processing unit 103 acquires accuracy testing results from the measuring unit 101 (Step D3).

Next, the data processing unit 103 determines whether or not the sensor use-by date has expired (Step D4). Specifically, the data processing unit 103 compares the sensor use-by date acquired in Step D2 and the current date and time to determine whether or not the current date and time is within the sensor use-by period. If the result of the determination made in Step D4 indicates that it has expired, the data processing unit 103 carries out Step D8.

On the other hand, if the result of the determination made in Step D4 indicates that it is still valid, the data processing unit 103 determines whether or not the reference solution use-by date is still valid (Step D5). Specifically, the data processing unit 103 compares the reference solution use-by date acquired in Step D2 and the current date and time to determine whether or not the current date and time is within the reference solution use-by period. If the result of the determination made in Step D5 indicates that it has expired, the data processing unit 103 carries out Step D8.

It should be noted that it is sufficient to set up the order of steps from Step D2 to Step D6, which is described below, such that Steps D4 and D5 are carried out after Step D2 and Step D6 is carried out after Step D3, and it is possible to change the order as long as these conditions are satisfied. For example, after carrying out Step D2, Step D4, and Step D5, the data processing unit 103 can carry out Step D3 and then Step D6. Alternatively, Step D5 may be carried out after executing Step D2, and Step D4 may be performed thereafter.

In addition, if the result of the determination made in Step D5 indicates that it is still valid, the data processing unit 103 determines whether or not the accuracy testing results obtained in Step D3 meet the preset conditions (Step D6). If the result of the determination made in Step D6 indicates that the accuracy testing results do not meet the preset conditions, the data processing unit 103 carries out Step D8.

Since the measuring unit 101 in Embodiment 3 is a glucometer, the blood glucose value being within a predetermined concentration range is suggested as the preset condition. This predetermined concentration range is set as appropriate in accordance with the specifications of the reference solution.

On the other hand, if the result of the determination made in Step D6 indicates that the results of accuracy testing meet the preset conditions, the data processing unit 103 determines that the quality control criteria have been met and displays a message to the effect that the quality control criteria have been met on the display screen (not shown) of the measuring device 100 (Step D7). Next, the data processing unit 103 exercises control such that the target component is measured by the measuring device 100 using a sensor 104 having a sample drop 106 applied thereto (Step D9). Specifically, the data processing unit 103 authorizes the measuring unit 101 to perform measurements using the sensor 104 and directs it to carry out measurements with the sensor 104. The execution of Step D9 concludes processing in the measuring device 100.

In addition, the data processing unit 103 determines in Step D8 that the quality control criteria have not been met, a message to the effect that the quality control criteria have not been met is displayed on the display screen (not shown) of the measuring device 100. Furthermore, in addition to such processing, the data processing unit 103 exercises control such that the measurement of the target component by the measuring device 100 with the sensor 104 having a sample drop 106 applied thereto is not carried out. Specifically, the data processing unit 103 disables the measurement functionality of the measuring unit 101. The execution of Step D8 also concludes processing in the measuring device 100.

In addition, the software program used in Embodiment 3 can be any software program as long as it causes a computer to execute Steps D1-D9 illustrated in FIG. 12. The measuring device 100 and quality control method used in Embodiment 3 can be implemented by installing and executing this software program on a computer. In this case, the CPU of the computer operates and performs processing as the data processing unit 103. In addition, a measuring unit connected to the computer operates as the measuring unit 101 and a code reading unit such as a barcode reader connected to the computer operates as the code reading unit 102.

As described above, in accordance with Embodiment 3, in case that faulty measurement results will be obtained, the operator of the measuring device 100 cannot perform measurements, thereby avoiding situations that produce faulty measurement results. In addition, when faulty measurement results were produced using the measuring device disclosed in Patent Documents 1 and 2, it was difficult to determine whether the problem stemmed from the measuring devices or whether there was a problem with the sensors and reference solutions. Embodiment 3, however, makes it possible to identify the reason in a simple manner.

Furthermore, although messages to the effect that the quality control criteria have been met and to the effect that the quality control criteria have not been met are outwardly communicated in Embodiment 3 by displaying them on the display unit, the outbound notifications are not limited to such implementations and may also be carried out using sounds, flashing lights, and the like. In particular, when communicating a message to the effect that the quality control criteria have not been met, it is preferable to perform outbound notification in the form of an alert.

In addition, in Embodiment 3, after the execution of Steps D8 and D9, the data processing unit 103 can identify, for example, the time that has elapsed after determining that the quality control criteria have been met and the number of times the measuring device 100 has carried out accuracy testing and can store the identified values in a storage unit (not shown). In such a case the management of the measuring device 100 is facilitated.

In addition, Embodiment 3 is not limited to the above-described implementation. For example, an implementation that employs codes representing sensor identification information used for identifying sensors is suggested as another implementation. In this implementation, the code reading unit 102 acquires sensor identification information. The data processing unit 103 then determines whether or not the sensor identified by the acquired sensor identification information can be used in the measuring unit 101. If the determination yields that the sensor can be used in the measuring unit 101, the data processing unit 103 directs the measuring unit 101 to carry out measurements using the sensor. On the other hand, if the determination yields that the sensor cannot be used in the measuring unit 101, the data processing unit 103 disables the measurement functionality of the measuring unit 101.

In addition, the data processing unit 103 exercises control intended to ensure that no measurement of the target component using the sensor 104 with a drop of the sample 106 applied thereto is performed in the measuring device 100, issues an outbound notification, or does both in the following cases. Specifically, this happens if at least one of the following is true: if the code reading unit 102 cannot acquire a sensor use-by date (Step D2 of FIG. 12); if the code reading unit 102 cannot acquire a reference solution use-by date (Step D2 of FIG. 12), and if the data acquisition unit 101 cannot acquire measurement data relating to the reference solution 107 (Step D3 of FIG. 12). In this case, the data processing unit 103 disables the measurement functionality of the measuring unit 101 and, in addition or instead of that, issues an alert to the operator.

Although the invention of the present application has been described above with reference to embodiments, the invention of the present application is not limited to the above-described embodiments. It will be appreciated by those of ordinary skill in the art that various changes in the form and details of the invention of the present application can be made within the scope of the invention of the present application.

Industrial Applicability

In accordance with the present invention, measurement data obtained using conventional measuring devices can be associated with data related thereto in a simple manner. The present invention is useful in data management at medical institutions and in product quality management at factories and the like.

DESCRIPTION OF REFERENCE NUMERALS 1-4 Luminous elements (LEDs: Light-emitting diodes)
10 Information acquisition device (Embodiment 1)
10a Mounting surface
11 Data acquisition unit
12 Code reading unit
12a Code reading surface
13 Data processing unit
14 Data storage unit
15 Input receiving unit
16 Display unit
16a Display screen
17, 18, 19 Clamping sections
20 Measuring device
21 Sensor strip insertion slot
22 Display screen
23 Plug-in opening for communication cable
24 Sensor strip to which a drop of sample is applied
25 Sensor strip to which a drop of reference solution is applied
26 Sample
27 Reference solution
30 Code table
31 Code
32 Information represented by code
40 Server computer
50 Docking station
51 Communication cable
60 Information acquisition device (Embodiment 2)
70 Measurement system (Embodiment 1)
71 Measurement system (Embodiment 2)
100 Measuring device
101 Measuring unit
102 Code reading unit
103 Data processing unit
104 Sensor strip to which a drop of sample is applied
105 Sensor strip to which a drop of reference solution is applied
106 Sample
107 Reference solution
108 Code

The invention claimed is:

1. An information acquisition device comprising:
   a data acquisition unit that is configured to acquire measurement data from an external measuring device;
   a code reading unit that is configured to read a code to acquire the information represented by the code; and
   a data processing unit that is configured to associate the information acquired by the code reading unit with the measurement data acquired by the data acquisition unit,
   wherein:
   the external measuring device is configured to perform measurement of a target component in a sample and accuracy testing of a reference solution used for the measurement of the target component with a sensor;
   the code includes a code representing a first use-by date set for the sensor and a code representing a second use-by date set for the reference solution; and
   where the code reading unit is configured to acquire the first use-by date and the second use-by date, and
   the data processing unit is configured to determine whether or not at least one of the first use-by date and second use-by date acquired by the code reading unit has expired; and to exercise control intended to ensure that no processing of the sample-related measurement data of an expired first use-by date and/or an expired second use-by date is performed in the information acquisition device, to issue an outbound notification, or to do both.

2. The information acquisition device according to claim 1, wherein:
   at least one type of code selected from the group consisting of a code representing an identifier that identifies a medical practitioner and a code representing an identifier that identifies a patient is used when the external measuring device is a medical measuring device used to measure patient status.

3. The information acquisition device according to claim 1, wherein:
the data acquisition unit is configured to acquire reference solution-related measurement data output by the measuring device during accuracy testing, and
the data processing unit is configured to further determines whether or not the reference solution-related measurement data meets preset conditions and to exercise control intended to ensure that no processing of the sample-related measurement data is performed in the information acquisition device, to issue an outbound notification, or to do both if the reference solution-related measurement data does not meet the preset conditions.

4. The information acquisition device according to claim 3, wherein:
the reference solution-related measurement data meets the preset conditions for unexpired first use-by and second use-by dates, and the data processing unit issues an outbound notification to that effect.

5. The information acquisition device according to claim 3, wherein:
the data processing unit is configured to exercise control intended to ensure that processing of the sample-related measurement data is carried out in the information acquisition device for unexpired first use-by and second use-by dates and, at the same time, the reference solution-related measurement data meets the preset conditions.

6. The information acquisition device according to claim 3, wherein:
the code reading unit cannot acquire the first use-by date, the code reading unit cannot acquire a second use-by date, the data acquisition unit cannot acquire the reference solution-related measurement data, or the data acquisition unit cannot acquire the sample-related measurement data,
with the result that the data processing unit is configured to exercise control intended to ensure that no processing of the sample-related measurement data is performed in the information acquisition device, to issue an outbound notification, or to do both.

7. The information acquisition device according to claim 1, wherein:
a code representing sensor identification information for identifying the sensor is used as the code,
the code reading unit acquires the sensor identification information,
the data processing unit is configured to determine whether or not the sensor identified by the acquired sensor identification information can be used in the measurement device, and to exercise control such that no processing of the sample-related measurement data is performed in the information acquisition device, to issue an outbound notification, or to do both if the sensor cannot be used in the measuring device.

8. The information acquisition device according to claim 1, wherein:
the information acquisition device is adapted to enable operation involving switching between operational modes including a quality control mode,
the operational mode is set to the quality control mode, and
the data processing unit is configured to determine whether or not at least one date selected from the first use-by date and the second use-by date acquired by the code reading unit has expired.

9. The information acquisition device according to claim 1, wherein:
the code reading unit cannot acquire the information,
with the result that the data processing unit associates dummy data with the measurement data acquired by the data acquisition unit.

10. The information acquisition device according to claim 1, wherein:
the code reading unit is configured to read a plurality of codes representing different information items to acquire the information represented by each respective code, and
the data processing unit is configured to associate the acquired plurality of information items with the measurement data.

11. The information acquisition device according to claim 10, wherein:
a plurality of barcodes are used as the codes and the number of digits in each one of the plurality of barcodes is determined by the type of information represented by the barcode.

12. The information acquisition device according to claim 1, further comprising an input receiving unit configured to receive external information input,
wherein the data processing unit is configured to associate information received by the input receiving unit with the measurement data.

13. A measurement system comprising a measuring device and the information acquisition device according to claim 1.

14. A method for utilizing a measuring device and a code representing specific information, comprising the steps of:
(a) acquiring measurement data from the measuring device us n the information acquisition device according to claim 1;
(b) reading the code and acquiring the information represented by the code; and
(c) associating the information acquired in step (b) with the measurement data acquired in step (a).

* * * * *